US012472299B2

(12) United States Patent
Tokuoka et al.

(10) Patent No.: US 12,472,299 B2
(45) Date of Patent: Nov. 18, 2025

(54) RESERVOIR ASSEMBLY FOR PROVIDING CARDIOPLEGIC SOLUTION CONTAINING BICARBONATE ION, AND METHOD FOR MANUFACTURING THE SAME

(71) Applicant: FUSO PHARMACEUTICAL INDUSTRIES, LTD., Osaka (JP)

(72) Inventors: Shogo Tokuoka, Osaka (JP); Yasushige Tanaka, Osaka (JP); Shin-ichi Inoue, Osaka (JP); Tomoko Mori, Osaka (JP)

(73) Assignee: FUSO PHARMACEUTICAL INDUSTRIES, LTD., Osaka (JP)

( * ) Notice: Subject to any disclaimer, the term of this patent is extended or adjusted under 35 U.S.C. 154(b) by 696 days.

(21) Appl. No.: 17/600,274

(22) PCT Filed: Apr. 3, 2020

(86) PCT No.: PCT/JP2020/015352
§ 371 (c)(1),
(2) Date: Dec. 14, 2021

(87) PCT Pub. No.: WO2020/204170
PCT Pub. Date: Oct. 8, 2020

(65) Prior Publication Data
US 2022/0203009 A1 Jun. 30, 2022

(30) Foreign Application Priority Data
Apr. 4, 2019 (JP) ................................ 2019-072219

(51) Int. Cl.
*A61J 1/10* (2006.01)
*A61K 9/08* (2006.01)
(Continued)

(52) U.S. Cl.
CPC .............. *A61M 1/3664* (2013.01); *A61J 1/10* (2013.01); *A61K 9/08* (2013.01); *A61K 33/00* (2013.01);
(Continued)

(58) Field of Classification Search
CPC ........ A61M 1/3664; A61M 2205/3327; A61M 2207/00; A61J 1/10; A61J 1/2093;
(Continued)

(56) References Cited

U.S. PATENT DOCUMENTS 5,462,524 A * 10/1995 Powell .................. A61K 33/30 424/614
6,232,128 B1 * 5/2001 Iguchi ....................... A61J 1/05 436/1
(Continued)

FOREIGN PATENT DOCUMENTS

| | | |
|---|---|---|
| CN | 1277547 | 12/2000 |
| JP | 5-49675 | 3/1993 |

(Continued)

OTHER PUBLICATIONS

International Search Report (ISR) issued Jun. 9, 2020 in International (PCT) Application No. PCT/JP2020/015352.
(Continued)

*Primary Examiner* — Susan S Su
*Assistant Examiner* — Erin A Kim
(74) *Attorney, Agent, or Firm* — Wenderoth, Lind & Ponack, L.L.P.

(57) ABSTRACT

The object of the invention is to provide a novel reservoir assembly for providing a cardioplegic solution and a method for manufacturing the same. An aspect of the invention is to provide a reservoir assembly for providing a cardioplegic solution, comprising a multi-chamber reservoir; a gas-impermeable outer package packaging the multi-chamber res-
(Continued)

ervoir; an oxygen detection agent and a deoxygenation agent in a space part between the multi-chamber reservoir and the outer package, wherein the deoxygenation agent neither generates nor absorbs carbon dioxide, wherein the multi-chamber reservoir comprises at least a first chamber, a second chamber, and a first separator wall that separates the two chambers, the first chamber holds a first medical liquid, the second chamber holds a second medical liquid containing bicarbonate ions, one or both of the first medical liquid and the second medical liquid contains potassium ions, the cardioplegic solution comprises the first medical liquid and the second medical liquid, and the cardioplegic solution contains bicarbonate ions of 5 to 20 mEq/L and potassium ions of 5 to 35 mEq/L. Another aspect of the invention is to provide a method for manufacturing the reservoir assembly for providing a cardioplegic solution.

10 Claims, 1 Drawing Sheet

(51) Int. Cl.

*A61K 33/00* (2006.01)
*A61K 33/14* (2006.01)
*A61M 1/36* (2006.01)
*B65D 81/32* (2006.01)

(52) U.S. Cl.

CPC .............. *A61K 33/14* (2013.01); *B65D 81/32* (2013.01); *A61J 2200/70* (2013.01); *A61M 2205/3327* (2013.01); *A61M 2207/00* (2013.01)

(58) Field of Classification Search

CPC ........ A61J 2200/70; A61J 1/05; A61J 1/1468; A61K 9/08; A61K 33/00; A61K 33/14; A61K 9/0019; B65D 81/32; B65D 81/18; A61P 9/00

See application file for complete search history.

(56) References Cited

U.S. PATENT DOCUMENTS

| | | | | |
|---|---|---|---|---|
| 6,248,258 | B1 | 6/2001 | Tomita et al. | |
| 2004/0123563 | A1 | 7/2004 | Inada et al. | |
| 2006/0118433 | A1 | 6/2006 | Nishio | |
| 2006/0154873 | A1 | 7/2006 | Sumiyoshi et al. | |
| 2006/0275742 | A1* | 12/2006 | Komeda ............ | A61K 31/7016 435/1.1 |
| 2007/0265593 | A1* | 11/2007 | Kitagawa ............ | A61M 1/1686 604/403 |
| 2011/0059177 | A1* | 3/2011 | Thatte ........................ | A61P 9/00 514/23 |
| 2018/0028401 | A1* | 2/2018 | Chen .......................... | A61J 1/10 |
| 2019/0350811 | A1* | 11/2019 | Malhotra .................. | B65B 3/04 |
| 2022/0088066 | A1* | 3/2022 | Chen ...................... | A61K 33/06 |

FOREIGN PATENT DOCUMENTS

| | | | | |
|---|---|---|---|---|
| JP | 2000-462 | | 1/2000 | |
| JP | 2000-308669 | | 11/2000 | |
| WO | 2004/010918 | | 2/2004 | |
| WO | 2004/108059 | | 12/2004 | |
| WO | WO-2004108059 | A1 * | 12/2004 | ............ A61J 1/2093 |
| WO | 2005/000190 | | 1/2005 | |
| WO | WO-2005000190 | A1 * | 1/2005 | ................ A61J 1/00 |
| WO | WO-2009105165 | A2 * | 8/2009 | ............. A61K 31/16 |
| WO | WO-2016171118 | A1 * | 10/2016 | ................ A61J 1/10 |

OTHER PUBLICATIONS

International Preliminary Report on Patentability and Written Opinion of the International Searching Authority issued Sep. 28, 2021 in International (PCT) Application No. PCT/JP2020/015352.

"Composition/Attributes", non-official translation (Mochida Pharmaceutical Co., Ltd. Cardiac Surgery Cardioplegic and Myocardial-Protective Liquid: Miotecter for Coronary Vessels), Apr. 2015, cited in ISR.

Communication pursuant to Rule 164(1) EPC issued Nov. 18, 2022 in corresponding European Patent Application No. 20784891.2.

Extended European Search Report issued Dec. 12, 2022 in corresponding European Patent Application No. 20784891.2.

* cited by examiner

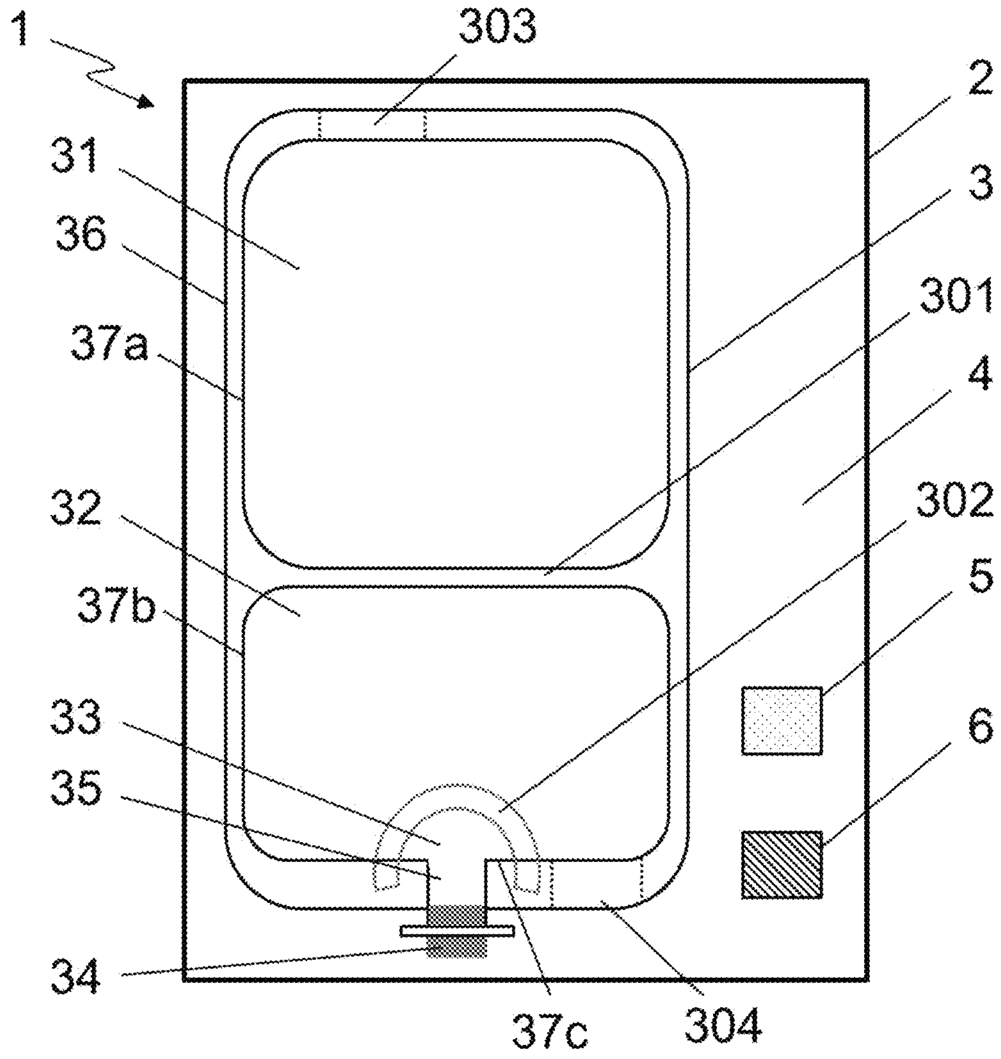
1
303
2
31
3
36
301
37a
4
32
302
37b
5
33
6
35
34
37c
304

RESERVOIR ASSEMBLY FOR PROVIDING CARDIOPLEGIC SOLUTION CONTAINING BICARBONATE ION, AND METHOD FOR MANUFACTURING THE SAME

TECHNICAL FIELD

The invention relates to a reservoir assembly for providing a cardioplegic solution containing bicarbonate ions and a method for manufacturing the same.

BACKGROUND

The heart is an organ that beats continuously from birth to death of an animal and circulates blood in the body. Cardiac surgery such as intracardiac repair may require to arrest pulsation for technical necessity. In the surgery, an artificial heart-lung (extracorporeal circulation) may be employed to support blood circulation and cardioplegia may be employed to protect myocardium.

Cardioplegia mostly arrests heart's electrical beats rapidly to preserve energy in myocardial cells. The myocardium's electrical beats consume most of the heart's energy. The cardioplegic liquid is used for this purpose.

The cardioplegic liquid is classified into blood cardioplegic solution containing blood components and crystalloid cardioplegic solution containing no blood components. The crystalloid cardiac solution is classified into extracellular fluid-type solution containing a high concentration of $Na^+$ and intracellular fluid-type solution containing a low concentration of $Na^+$. St. Thomas' solution and Tyers' solution are exemplified as the extracellular fluid-type solution. Brettschneider's solution is exemplified as the intracellular fluid-type solution. St. Thomas' II solution is also known as one of the crystalloid cardioplegic solutions and was produced by adding bicarbonate ions in St. Thomas' solution to impart the buffering effect. St. Thomas' II solution is provided a kit named Miotecter® Coronary Vascular Injection (Kyowa CritiCare Co., Ltd.). The kit (hereinafter referred to as "Miotecter® cardioplegic solution kit") comprises a first medical liquid held in a plastic bottle and a second medical liquid containing carbonate ions held in a glass vial. The two liquids are mixed just before use to provide the cardioplegic solution.

The Miotecter® cardioplegic solution kit has a glass vial (also called ampule) that holds the second medical liquid containing bicarbonate ions. The glass vial can retain carbon dioxide gas (carbon dioxide) generated from bicarbonate ions in the container to stabilize pH of the medical liquid. When a gas-permeable type container holds the second medical liquid, carbon dioxide gas generated from the bicarbonate ions leaks from the container, thereby increases the pH of the second medical liquid. A medical solution produced with a second medical liquid having an increased pH may cause side effects in a subject who receives the medical solution. Accordingly, glass vials are advantageous for a medical liquid containing volatile bicarbonate ions.

However, glass containers are generally heavier than plastic containers (Patent Literature 1). When a glass container and a plastic container are provided in a kit, the glass container may be small to decrease the kit's weight in total. The Miotecter® cardioplegic solution kit has a glass container (ampule) for the second medical liquid of 5 mL and a plastic container for the first medical liquid of 495 mL. The second medical liquid (5 mL) in the glass container is added to the first medical liquid (495 mL) in the plastic container to provide the medical solution. Due to the volume ratio being 1:99, it is hard to judge whether the second medical liquid is added to the liquid in the plastic container by appearances, which may cause a risk of mixing twice or forgetting to mix. The risk gets more severe in dealing with multiple kits for Miotecter® cardioplegic solution kit at once.

Glass containers are fragile compared to plastic containers. Bits of glass are generally sharp and easily hurt the user's fingers (Patent Literature 1). For example, when cutting the glass container (ampule) and taking out the second medical liquid from the cut ampule, the users may hurt their fingers at the sharp edge of the cut ampule. The users might risk mistakenly sticking their fingers with a needle when inserting the needle into the glass container to take out the second medical liquid. These risks led to a tendency in medical sites to avoid using glass containers to bring safety to medical staff who needs to respond quickly. There was also a need for a medical formulation not required to dispense and mix the liquids at the time of use.

CITATION LIST

Patent Literature 1: JP 1993-049675 A

SUMMARY

Dialysis solutions or substitution solutions containing bicarbonate ions have been made into a reservoir assembly product that contains a plastic multi-chamber reservoir (e.g., Fuso Pharmaceutical Industries, Ltd., "Sublood®-BSG"). The plastic multi-chamber reservoir holds two medical liquids in its chambers, respectively, which are mixed to provide a dialysis solution or isotonic electrolyte solution containing bicarbonate ions. However, any reservoir assembly product that has a plastic multi-chamber reservoir for providing cardioplegic solutions containing bicarbonate ions have not been available.

The cardioplegic solution is a medical liquid developed to reduce myocardium injuries during cardiac arrest. In general, the cardioplegic solution rapidly arrests the heart due to depolarization induced by its high concentration of potassium ions, thereby suppressing energy consumption in the heart. The cardioplegic solution can be used at a low temperature to reduce the metabolism rate in the heart and is supplied with a drug to suppress myocardium damages caused by ischemia during cardiac arrest. On the other hand, the dialysis solution or isotonic electrolyte solution is a medical liquid used to maintain the homeostasis of a living body in blood purification therapy, including continuous blood filtration and hemodialysis. Due to the difference in the purposes of use, their liquids differ in the balance of bicarbonate ions, sodium ions, potassium ions, magnesium ions, and calcium ions.

For example, a bicarbonate ions-containing dialysis solution or isotonic electrolyte solution contains sodium ions ($Na^+$) of 130 to 145 mEq/L, potassium ions ($K^+$) of 2 to 5 mEq/L, calcium ions ($Ca^{2+}$) of 2 to 5 mEq/L, magnesium ions ($Mg^{2+}$) of 0.5 to 2.5 mEq/L, chloride ions ($Cl^-$) of 90 to 130 mEq/L, bicarbonate ions ($HCO_3^-$) of 20 to 35 mEq/L, citrate ions of 1 to 7 mEq/L, and glucose of 0 to 5 g/L (JP 2007-301205 A).

St. Thomas' II solution, which is a cardioplegic solution, contains sodium ions ($Na^+$) of 120 mEq/L, potassium ions ($K^+$) of 16 mEq/L, calcium ions ($Ca^{2+}$) of 2.4 mEq/L, magnesium ions ($Mg^{2+}$) of 32 mEq/L, chloride ions (CL) of 160.4 mEq/L, and bicarbonate ions ($HCO_3^-$) of 10 mEq/L. St. Thomas' II solution has a pH of 7.6 to 8.0.

Thus, the cardioplegic solution contains electrolytes whose concentrations are significantly different from conventional dialysis solutions or isotonic solutions. For example, the cardioplegic solution contains magnesium ions of 32 mEq/mL, which are about ten times higher than magnesium ion concentrations of 2 to 5 mEq/L in conventional dialysis or isotonic solutions. The cardioplegic solution contains bicarbonate ions of 10 mEq/mL, which are about two to three times lower than bicarbonate ion concentrations of 20 to 35 mEq/mL in conventional dialysis or isotonic solutions. The magnesium ion may form insoluble particles with the bicarbonate ion in a liquid having an alkaline pH. A liquid whose bicarbonate ion concentration is relatively low tends to be alkaline due to a low buffering capacity against an increase of pH after the leak of carbon dioxide generated from bicarbonate ions in the liquid. There was no guidance to provide a liquid formulation whose bicarbonate ion concentration is relatively low in a stable manner. Accordingly, there was no guidance to provide a reservoir assembly for providing a medical solution whose bicarbonate ion concentration is relatively low in a stable manner with a plastic container whose gas retaining property is significantly different from that of a glass container. The object of the invention is to provide a novel reservoir assembly for providing a cardioplegic solution and a method for manufacturing the same.

Solution to Problem

The invention provides the following reservoir assembly for providing a cardioplegic solution and a method for manufacturing the same:

A reservoir assembly for providing a cardioplegic solution, comprising a multi-chamber reservoir; a gas-impermeable outer package packaging the multi-chamber reservoir; an oxygen detection agent in a space part between the multi-chamber reservoir and the outer package; and a deoxygenation agent in the space part, wherein the deoxygenation agent neither generates nor absorbs carbon dioxide, wherein the multi-chamber reservoir comprises at least a first chamber, a second chamber, and a first separator wall that separates the two chambers; the first chamber holds a first medical liquid; the second chamber holds a second medical liquid containing bicarbonate ions; one or both of the first medical liquid and the second medical liquid contains potassium ions; the cardioplegic solution comprises the first medical liquid and the second medical liquid; and the cardioplegic solution contains bicarbonate ions of 5 to 20 mEq/L and potassium ions of 5 to 35 mEq/L.

A method for manufacturing a reservoir assembly for providing a cardioplegic solution, the method comprising: sterilizing a multi-chamber reservoir comprising at least a first chamber that holds a first medical liquid, a second chamber that holds a second medical liquid containing bicarbonate ions, and a first separator wall that separates the two chambers; packaging the multi-chamber reservoir, an oxygen detection agent, and a deoxygenation agent in a gas-impermeable outer package, wherein the deoxygenation agent neither generates nor absorbs carbon dioxide; filling carbon dioxide into the outer package; and sealing the outer package after filling carbon dioxide; wherein one or both of the first medical liquid and the second medical liquid contains potassium ions; the cardioplegic solution comprises the first medical liquid and the second medical liquid; and the cardioplegic solution contains bicarbonate ions of 5 to 20 mEq/L and potassium ions of 5 to 35 mEq/L.

BRIEF DESCRIPTION OF DRAWINGS

FIG. 1 is a schematic drawing showing a reservoir assembly according to an embodiment of the invention.

DESCRIPTION OF EMBODIMENTS

A "multi-chamber reservoir" in the specification means a pharmaceutically acceptable container that comprises at least two chambers for holding a medical liquid. The container has an outside wall made from a material that is, for example, gas-permeable but liquid-impermeable and resistant to sterilization with steam under high pressure. The material for the outside wall of the multi-chamber reservoir includes, but is not limited to, synthetic resin (plastics) conventionally used in the pharmaceutical field, for example, polyolefin resin such as polypropylene and polyethylene, and polyvinyl chloride resin. The multi-chamber reservoirs are commercially available and can be manufactured according to known methods.

The multi-chamber reservoir comprises at least two chambers (in the outside wall) that are defined by inner surface. A part of the inner surface may also constitute the outside wall. A part or all of the inner surface, which define the at least two chambers, form a separator wall that separates the two chambers. The separator wall may be, but is not limited to, an adhesive or welded part that can be peeled off or opened by handling the multi-chamber reservoir from the outside. The adhesive or welding strength of the separator wall is smaller than the outside wall of the multi-chamber reservoir or inner surface of the chambers, or the adhesive or welding parts in other walls of the multi-chamber reservoir. The separator walls may be formed with different adhesive agents or under different welding conditions from those used for forming, for example, the outside wall of the multi-chamber reservoir, other walls such as the inner surface defining the chambers. Opening the separator wall allows to contact and mix the medical liquids held in the chambers.

The multi-chamber reservoir is provided with, for example, a port part that allows injecting liquid in the reservoir. The port part is connected to, for example, one chamber of the at least two chambers of the multi-chamber reservoir so that it allows liquid to flow through in and out. The port part is hermetically closed, for example, with a plug not to flow liquid through. Plugs are made from, for example, synthetic resins conventionally used in the pharmaceutical field. The material for plugs includes, but is not limited to, natural resin (for example, natural rubber) and synthetic resin (for example, elastomer) conventionally used in the pharmaceutical field.

A "gas-impermeable outer package" in the specification means a package whose gas permeability rate is low and whose size and shape allow to pack the multi-chamber reservoir. The gas-impermeable outer packages are made of, for example, carbon dioxide-impermeable thermoplastics. The materials for gas-impermeable outer packages may include, for example, ethylene-vinyl alcohol copolymer (EVOH), polyethylene terephthalate (PET), polyvinylidene chloride (PVDC), nylon (NY), and the like; multilayer material (e.g., PET/NY/EVOH) in which the above materials are laminated; vapor deposition material in which amorphous carbon, silicon oxide, metal such as aluminum oxide, or inorganic material are deposited on the above materials;

or multilayer material in which aluminum foils are laminated. The gas-impermeable outer packages are commercially available and can be manufactured according to known methods.

A "low gas-permeability rate" in the context of the gas-impermeable outer package means an oxygen-permeability rate of no more than 20 [$cm^3/m^2 \cdot 24$ h·atm]. The oxygen-permeability rate of the gas-impermeable outer package is preferably no more than 15, more preferably no more than 10, and still more preferably no more than 5. For example, the oxygen-permeability rate of the gas-impermeable outer package is preferably no more than 5, more preferably no more than 3, still more preferably no more than 2, even more preferably no more than 1. For example, the oxygen-permeability rate of the gas-impermeable outer package is no more than 1. The oxygen-permeability rate in the specification is measured according to the JIS K7126-2 (Equal-pressure method).

A "deoxygenation agent that neither generates nor absorbs carbon dioxide" in the specification means a deoxygenation agent that does not substantially change carbon dioxide concentration in a system under a predetermined condition. "Does not substantially change carbon dioxide concentration in a system under a predetermined condition" in the specification means a reaction in which substantially no carbon dioxide is generated or absorbed in a system under the predetermined condition. The deoxygenation agent that does not substantially change the carbon dioxide concentration in a system under the predetermined condition is, for example, a deoxygenation agent that is not involved in a reaction generating or absorbing carbon dioxide in a system in which oxygen is absorbed. The deoxygenation agent that neither generates nor absorbs carbon dioxide only changes the carbon dioxide concentration by no more than 0.3%, preferably no more than 0.2% or more preferably no more than 0.1% in a gas-impermeable outer package placed under normal pressure at room temperature for one week when the deoxygenation agent is packed in the gas-impermeable outer package filled with 4.4 volumes of 2.5% carbon dioxide gas (a mixed gas containing 2.5% $CO_2$ and 97.5% $N_2$) and 1 volume of air and sealed. The carbon dioxide concentration may be determined by infrared absorption spectrum. A device for measuring a carbon dioxide concentration based on infrared absorption spectrum may be an $O_2/CO_2$ analyzer (Dansensor Co. Ltd., CheckMate 3).

The deoxygenation agent that neither generates nor absorbs carbon dioxide may be, for example, a deoxygenation agent that comprises a cross-linked polymer having carbon-carbon unsaturated bonds as the main component (deoxygenation component). The deoxygenation component having carbon-carbon unsaturated bonds includes, for example, polyisoprene, polybutadiene, olefin-diene copolymer, diene oligomer, or partially hydrogenated polymer. Cross-linked polymer compounds include, but are not limited to, polymers having various covalent bonds (e.g., C—C, C—O, and C—N). The deoxygenation agent may be deoxygenation agents described in JP H11-34799 A or JP 2000-462 A. The deoxygenation agent may be manufactured according to the methods described in the documents.

An "oxygen detection agent" in the specification means a reagent that does not substantially react with gases other than oxygen gas and whose physical properties change by oxygen. Gases other than oxygen gas include, but are not limited to, carbon dioxide gas. For example, "does not substantially react with gases other than oxygen gas" means that an oxygen detection agent does not contain any components that absorb or release carbon dioxide. A reagent that does not substantially react with gases other than oxygen gas could contain a component known to react with carbon dioxide at an amount that does not interfere with the object of the present invention. The oxygen detection agent may change the carbon dioxide concentration in a gas-impermeable outer package by no more than 0.3%, preferably no more than 0.2% or more preferably no more than 0.1% when the gas-impermeable outer package is filled with 4.4 volumes of 2.5% carbon dioxide gas (a mixed gas containing 2.5% $CO_2$ and 97.5% $N_2$) and 1 volume of air and sealed, and is placed under normal pressure at room temperature for one week. The carbon dioxide concentration is determined by infrared absorption spectrum. A device for measuring a carbon dioxide concentration based on infrared absorption spectrum may be an $O_2/CO_2$ analyzer (Dansensor Co. Ltd., CheckMate 3).

The oxygen detection agent is, but is not limited to, a reagent that changes, for example, its color by oxygen. The oxygen detection agent includes, but is not limited to, a reductant, a basic substance, and an oxidation-reduction pigment showing different colors in oxidation and reduction states. Reductants include, but are not limited to, reducing saccharides. The reducing saccharides may be, for example, D-mannose, D-glucose, and D-erythrose either alone or in combination thereof. Basic substances include, but are not limited to, alkali metal carbonates and alkaline-earth metal carbonates. Oxidation-reduction pigments may be, but are not limited to, methylene blue, Raus violet, and methylene green either alone or in combination thereof. The oxygen detection agent is, for example, Ageless Eye produced by Mitsubishi Gas Chemical Company, Inc. The oxygen detection agents are commercially available and can be manufactured according to known methods.

A "cardioplegic solution" in the specification means a medical solution containing bicarbonate ions, which can induce arresting heart's beats (cardiac arrest) and protect the myocardium under ischemia. The cardioplegic solution has, for example, pH 5 to 8, preferably pH 6 to 8, more preferably pH 7 to 8, still more preferably pH 7.6 to 8, or pH 7.8. The cardioplegic solution is used, for example, at low temperatures (e.g., 4 to 8° C.) to reduce the metabolism rate in the heart. The cardioplegic solution has pH 7 to 8, preferably pH 7.7 to 7.9, more preferably pH 7.8 when used at low temperatures. The cardioplegic solution may be injected according to known methods. The cardioplegic solution is injected using, for example, a conventional cardioplegic solution supplying circuit.

The cardioplegic solution includes, but is not limited to, various ion species and other components. Ion species include, but are not limited to, potassium ion and bicarbonate ion and further include at least one ion species selected from the group consisting of sodium ion, calcium ion, magnesium ion, and chloride ion. The ion species can be obtained, for example, by dissolving pharmaceutically acceptable salts (electrolytes) that dissociate to give ion species in an aqueous solution. Pharmaceutically acceptable salts are commercially available. Ion species in solution can be measured according to known methods (e.g., Japanese Pharmacopoeia general test procedures). Other ingredients in the cardioplegic solution include, but are not limited to, saccharides such as glucose and mannitol, local anesthetics such as lidocaine and procaine, vasodilators such as adenosine and nitric oxide, calcium antagonists, and nitrites.

The "sodium ion" is a component, for example, for keeping the ion balance with blood (extracellular fluid). Sodium ions are obtained, for example, by dissolving salts such as sodium chloride or sodium bicarbonate in an aqueous solution. The cardioplegic solution contains, for example, sodium ions of 100 to 150 mEq/L, preferably 110 to 130 mEq/L, more preferably 115 to 125 mEq/L, still more preferably 120±3 mEq/L.

The "potassium ion" is a component, for example, for inducing cardiac arrest rapidly to protect the myocardium under ischemia. Potassium ions are obtained, for example, by dissolving salts such as potassium chloride in an aqueous solution. The cardioplegic solution contains, for example, potassium ions of 5 to 35 mEq/L, preferably 8 to 25 mEq/L, more preferably 10 to 20 mEq/L, still more preferably 14 to 17 mEq/L, 15±0.5 mEq/L, or 16±0.5 mEq/L.

The "calcium ion" is a component, for example, for keeping normal permeabilities of the cell membrane under ischemia to prevent calcium paradox during reperfusion. Calcium ions are obtained, for example, by dissolving calcium chloride hydrate in an aqueous solution. The cardioplegic solution contains, for example, calcium ions of 0.5 to 5 mEq/L, preferably 2 to 4 mEq/L, more preferably 2 to 3 mEq/L, still more preferably 2.4±0.2 mEq/L.

The "magnesium ion" is a component, for example, for preventing flowing calcium into and magnesium and potassium out from myocardium cells to protect the myocardium. Magnesium ions are obtained, for example, by dissolving magnesium chloride hydrate in an aqueous solution. The cardioplegic solution contains, for example, magnesium ions of 2 to 55 mEq/L, preferably 15 to 45 mEq/L, more preferably 20 to 40 mEq/L, still more preferably 30 to 35 mEq/L, or 32±1 mEq/L.

A cardioplegic solution contains, for example, magnesium ions of 15 to 45 mEq/L, more preferably 20 to 40 mEq/L, still more preferably 30 to 35 mEq/L, or 32±0.5 mEq/L when the cardioplegic solution contains potassium ions of no less than 10 mEq/mL. A cardioplegic solution contains, for example, magnesium ions of 40 to 55 mEq/L, preferably 45 to 55 mEq/L, more preferably 50±1 mEq/L, when the cardioplegic solution contains potassium ions of less than 10 mEq/mL.

The "chloride ion" is a component, for example, for keeping the balance with blood. Chloride ions are obtained, for example, by dissolving salts such as sodium chloride, potassium chloride, magnesium chloride, and calcium chloride in an aqueous solution. The cardioplegic solution contains, for example, chloride ions of 100 to 180 mEq/L, preferably 130 to 170 mEq/L, more preferably 150 to 170 mEq/L, still more preferably 160.4±5 mEq/L.

The "bicarbonate ion" (also called "hydrogen carbonate ion") is a component, for example, for adjusting the medical liquid to weak alkaline similar to the blood and imparting buffering effect to the medical liquid to enhance the protective effect on myocardium. Bicarbonate ions are obtained, for example, by dissolving salts such as sodium bicarbonate in an aqueous solution. The cardioplegic solution contains, for example, carbonates ions of 5 to 20 mEq/L, preferably 8 to 18 mEq/L, more preferably 8 to 12 mEq/L, still more preferably 9 to 11 mEq/L, or 10±0.5 mEq/L.

A "pharmaceutical solution" means an aqueous solution containing various pharmaceutically acceptable ion species and optionally other components. Pharmaceutical solutions can be prepared according to known methods. Pharmaceutical solutions can be prepared, for example, by dissolving electrolytes and optionally other components that dissociate to give various ion species in water or aqueous solution. In the present invention, the cardioplegic solution can be prepared by combining, for example, by mixing at least two medical liquids. When the cardioplegic solution is prepared by combining a medical liquid containing bicarbonate ions with another medical liquid, one or both of calcium ion and magnesium ion should be included in the medical liquid containing no bicarbonate ion to prevent the formation of insoluble salts or fine particles (calcium carbonate or magnesium carbonate). A prepared pharmaceutical solution may be sterilized, for example, by filtration or sterilization with steam under high pressure.

For example, one of at least two medical liquids may be adjusted for the pH so that the cardioplegic solution prepared by mixing the liquids has a predetermined pH (for example, pH 7.6 to 8.0). The pH may be adjusted, for example, by adding dilute hydrochloric acid or sodium hydroxide. The pH may be adjusted, for example, by adding dilute hydrochloric acid to a medical liquid containing no bicarbonate ion. The medical liquid containing no bicarbonate ion is adjusted, for example, to pH 3.0 to 4.8, preferably pH 3.6 to 4.0, more preferably pH 3.8±0.1. Pharmaceutical solutions may be, for example, filtered, filled into a multi-chamber reservoir, and then further sterilized with steam under high pressure (e.g., 118° C., 16 minutes).

The multi-chamber reservoir is packed after sterilizing into a gas-impermeable outer package, for example, together with an oxygen detection agent and a deoxygenation agent that neither generates nor absorbs carbon dioxide. For example, carbon dioxide is filled into the space part between the multi-chamber reservoir and the outer package in an amount so as to supply bicarbonate ions equal to carbon dioxide released at the sterilization. The carbon dioxide may be filled as a mixed gas that contains other gases such as nitrogen gas.

In one example, carbon dioxide is filled into the space part in an amount so as to achieve the following: The bicarbonate ion concentration in a second medical liquid (dissolved carbon dioxide) after reaching an equilibrium with the carbon dioxide concentration in the space part (carbon dioxide in vapor phase) in the multi-chamber reservoir is within 100±2%, preferably 100±1.5%, more preferably 100±1% of the predetermined bicarbonate ion concentration in the second medical liquid before being sterilized. Concentrations of the bicarbonate ion are measured, for example, by liquid (ion) chromatography. For example, the bicarbonate concentration can be measured by liquid chromatography with a column of PCI-305S (6 μm 8.0 mm ID×300 mm). The term to reach an equilibrium between the dissolved carbon dioxide concentration and the carbon dioxide concentration in the vapor phase depends on, for example, the material forming the multi-chamber reservoir. The term may be one week or two or more weeks after manufacturing the reservoir assembly.

In one example, carbon dioxide is filled into the space part in an amount that the bicarbonate ion concentration after reaching an equilibrium between the dissolved carbon dioxide concentration and carbon dioxide concentration in the vapor phase is within 100±2%, 100±1.5%, or 100±1% of the predetermined bicarbonate ion concentration before being sterilized and the cardioplegic solution prepared with a second medical liquid containing bicarbonate ions has a pH in the predetermined pH range (e.g., 7.6 to 8.0).

In one example, carbon dioxide is filled into the space part between the multi-chamber reservoir and the gas-impermeable outer package, for example, as a mixed gas that contains nitrogen and 1 to 7%, 1 to 6%, or 1 to 5% of carbon dioxide, in a volume 1 to 4 times, 1 to 3 times, or 1 to 2 times the volume of the second medical liquid containing bicarbonate ions.

In one example, carbon dioxide is filled into the space part, for example, in an amount so as to achieve the following: The concentration of carbon dioxide gas (carbon dioxide) in the space part is 0.1 to 5%, preferably 0.2 to 2.5%, more preferably 0.3 to 1.5% after the dissolved carbon dioxide in the second medical liquid reaches an equilibrium with the carbon dioxide in the vapor phase. In this example, the pharmaceutical solution preferably has a pH within the predetermined pH range.

A chamber connected with a port part to allow flowing liquid through in and out holds, for example, a medical liquid whose sodium ions (135 to 146 mEq/mL) and potassium ions (3.5 to 5.0 mEq/L) are within the standard ion concentrations in serum (plasma) and whose osmotic pressure is 275 to 300 mOsm/kg (the ratio of the osmotic pressure (to physiological saline solution) is about 1). In this example, even if the medical liquid, whose ion concentrations are within the serum standard ion concentrations and whose osmotic pressure ratio is 1, is injected into a subject without opening the separator wall that separates the respective medical liquids in the multi-chamber reservoir, the injection may minimize adverse effects on the subject. The example is preferable from the viewpoint of fail-safe.

Embodiment 1

FIG. 1 shows a schematic diagram of a reservoir assembly according to an embodiment of the present invention.

The reservoir assembly 1 comprises a gas-impermeable outer package 2; a multi-chamber reservoir 3 packed in the outer package; and an oxygen detection agent 5 and a deoxygenation agent 6 in the space part 4 between the outer package and the multi-chamber reservoir; wherein the deoxygenation agent neither generates nor absorbs carbon dioxide. The multi-chamber reservoir 3 comprises an outside wall 36, which surrounds a first chamber 31, a second chamber 32, and a third chamber 33.

A first separator wall 301 separates the first chamber 31 and the second chamber 32. The first separator wall 301 constitutes a part of the inner surface 37*a* defining the first chamber 31 and a part of the inner surface 37*b* defining the second chamber 32.

A second separator wall 302 separates the second chamber 32 and the third chamber 33. The second separator wall 302 constitutes a part of the inner surface 37*b* defining the second chamber 32 and a part of the inner surface 37*c* defining the third chamber 33.

The multi-chamber reservoir 3 includes a port part 35 that allows liquid to flow through in and out of the third chamber 33. A plug 34 hermetically closes the port part 35.

Users check the color of the oxygen detection agent 5 before or immediately after opening the gas-impermeable outer package 2 of the reservoir assembly 1. The oxygen detection agent 5 is pink under less than 0.1% oxygen and blue under more than 0.5% oxygen at room temperature. The oxygen detection agent 5 changes its color within ten minutes after contacting air.

Users may take out and use the 1 L-volume multi-chamber reservoir 3 when the color of the oxygen detection agent 5 is pink. When the color is blue, it indicates that a pinhole occurs on the outer package 2. The user should not use the reservoir assembly 1 from the viewpoint of the stability of the medical solution. When a pinhole occurs on the outer package 2, carbon dioxide generated from bicarbonate ions in the second medical liquid, described below, releases from the space part 4 between the outer package 2 and the multi-chamber reservoir 3 to the outside of the outer package 2. As a result, the equilibrium between the bicarbonate ions in the second medical liquid and carbon dioxide in the space part 4 shifts toward generating carbon dioxide from bicarbonate ions, thereby increases the pH of the second medical liquid. A cardioplegic solution, produced with a second medical liquid of an increased pH, may have an alkalic pH than the desired pH. Injection of a cardioplegic solution of such an alkalic pH may cause a side effect in a subject and cannot achieve the desired effect.

The deoxygenation agent 6 that neither generates nor absorbs carbon dioxide can absorb oxygen in the space part 4, thereby decreasing the oxygen concentration to less than 0.1% in the space part 4.

The first chamber 31 holds the first medical liquid (pH3.8) 700 mL containing sodium ions of 108.9 mEq/L, potassium ions of 21.1 mEq/L, calcium ions of 3.4 mEq/L, magnesium ions of 45.7 mEq/L, and chloride ions of 179.1 mEq/L.

The second chamber 32 holds the second medical liquid 300 mL containing sodium ions of 146 mEq/L, potassium ions of 4 mEq/L, chloride ions of 116.7 mEq/L, and bicarbonate ions of 33.3 mEq/L. The second medical liquid has an osmotic pressure of 275 to 300 mOsm/kg and the standard ion concentrations in serum (plasma) (sodium ion standard range of 135 to 146 mEq/mL and potassium ion standard range of 3.5 to 5.0 mEq/mL). In this embodiment, the first medical liquid is held in the first chamber 31 distal from the port part 35. Even if the second medical liquid is injected through the port part 35 to a subject before being mixed with the first medical liquid, the injection of the second medical liquid is expected to cause fewer damages to the subject's heart.

The third chamber 33 is a safety space part to prevent the second medical liquid from being injected into a subject through the port part 35 before the first separator wall is opened. In this embodiment, the third chamber 33 does not hold liquid.

Pressing the first chamber 31 peels off or opens the first separator wall 301 and allows mixing the first medical liquid with the second medical liquid. Mixing the first medical liquid with the second medical liquid provides a cardioplegic solution (mixed solution).

The second separator wall 302 is sealed with higher adhesive or welding strength than the first separator wall 301 (adhesive or welding strength of the first separator wall<adhesive or welding strength of the second separator wall). Even if the second chamber 32 is pressed, the first separator wall 301 opens before the second separator wall 302 due to the strength difference. The second medical liquid can be mixed with the first medical liquid to provide the cardioplegic solution. Then, the second separator wall 302 opens.

Further pressing opens the second separator wall 302 after the first separator wall 301. The open of the second separator wall 302 allows the cardioplegic solution to enter the port part 35 and contact a plug 34. The cardioplegic solution enters a myocardium protection circuit through a needle inserted into the plug 34 and is injected into a subject (the heart).

The number of the medical liquids to be used for providing the cardioplegic solution is not limited. Embodiment 1 provides the cardioplegic solution prepared with the two medical liquids. A cardioplegic solution may be prepared, for example, with three medical liquids. In this case, a multi-chamber reservoir 3 comprises at least a corresponding number of chambers.

The volume of the multi-chamber reservoir 3 is not limited. Embodiment 1 uses the multi-chamber reservoir 3 of 1 L. The volume of a multi-chamber reservoir 3 may be, but is not limited to, 0.1 L or 3 L. The number of chambers included in the multi-chamber reservoir 3 is not limited. Embodiment 1 uses the multi-chamber reservoir 3 having three chambers. A multi-chamber reservoir 3 may comprise, for example, two, four, and more chambers.

The numbers of the oxygen detection agent 5 and the deoxygenation agent 6 used are not limited. Embodiment 1 uses one oxygen detection agent 5 and one deoxygenation agent 6 that neither generates nor absorbs carbon dioxide in the outer package 2. A plurality of deoxygenation agents 6 and oxygen detection agents 5 may be used. The formulations of the oxygen detection agent 5 and the deoxygenation agent 6 are not limited. The outer package 2 includes the oxygen detection agent 5 and the deoxygenation agent 6 as physically separated formulations. An oxygen detection agent 5 and a deoxygenation agent 6 may be used as a physically single formulation.

The type of the oxygen detection agent 5 is not limited. Embodiment 1 uses the oxygen detection agent 5 that changes its color. The type of a deoxygenation agent 6 is not limited. Embodiment 1 uses a deoxygenation agent 6 in the space part 4 that can decrease the oxygen to less than 0.1%

It is not limited which chamber holds which medical liquid. In Embodiment 1, the second chamber 32 proximal to the port part 35 holds the second medical liquid containing bicarbonate ions. A first chamber 31 distal from the port part 35 may hold a second medical liquid containing bicarbonate ions.

The combination of ion species and concentrations are not limited. In Embodiment 1, the first medical liquid and the second medical liquid respectively contain specific ion species at specific concentrations. When at least two medical liquids are a first and second medical liquids, they may contain each ion species without particular limitation as long as a desired cardioplegic solution can be produced by mixing the first and second medical liquids. When a second medical liquid contains magnesium and/or calcium ions in addition to bicarbonate ions, insoluble salts or particles may form. Magnesium and/or calcium ions are preferably added to a liquid different from the second medical liquid containing bicarbonate ions.

The ion species contained in respective medical liquids are not limited. In Embodiment 1, the first medical liquid contains both calcium and magnesium ions. In one example, at least two medical liquids do not contain one or both calcium and magnesium ions. In another example, a medical liquid of at least two medical liquids contains bicarbonate ions, and the other medical liquids contain one or both calcium ions and magnesium ions. In the example, one medical liquid contains bicarbonate ions, another medical liquid contains calcium ions, and the other medical liquid contains magnesium ions.

The ion species contained in the respective liquids are not limited. In Embodiment 1, the first and second medical liquids both contain sodium and potassium ions. In one example, at least two medical liquids for providing a cardioplegic solution do not contain sodium ions other than sodium ions as counterion of the other ion species such as bicarbonate ions. In another example, at least two medical liquids contain potassium and sodium ions in an amount so that a cardioplegic solution prepared with the liquids can contain potassium and sodium ions at a predetermined concentration. For example, a first medical liquid contains sodium ions, potassium ions, calcium ions, magnesium ions, and chloride ions, and a second medical liquid contains sodium ions, potassium ions, chloride ions, and bicarbonate ions.

The ion species and their amount in the respective liquids are not limited. In Embodiment 1, the cardioplegic solution prepared with the first medical liquid and the second medical liquid contains sodium ions of 120 mEq/L, potassium ions of 16 mEq/L, calcium ions of 2.4 mEq/L, magnesium ions of 32 mEq/L, chloride ions of 160.4 mEq/L, and bicarbonate ions of 10 mEq/L.

For example, a cardioplegic solution contains sodium ions of 100 to 150 mEq/L, potassium ions of 5 to 35 mEq/L, calcium ions of 0.5 to 5 mEq/L, magnesium ions of 2 to 55 mEq/L, chloride ions of 100 to 180 mEq/L, and bicarbonate ion of 5 to 20 mEq/L.

In Embodiment 1, the volume ratio of the first medical liquid to the second medical liquid is, but is not limited to, 7:3. The volume ratio of the first medical liquid to the second medical liquid may be, for example, 1:4 to 4:1, preferably 1:1 to 4:1, more preferably 2:1 to 3:1.

In Embodiment 1, the first medical liquid has, but is not limited to, a pH of 3.8. For example, a first medical liquid may be adjusted to pH of 3.0 to 4.8, preferably 3.6 to 4.0, more preferably 3.8±0.1 or not be adjusted for pH.

In Embodiment 1, the first and second medical liquids contain just sodium ions, potassium ions, calcium ions, bicarbonate ions, and chloride ions. The ion species contained in the respective liquids are not specifically limited. Depending on the purpose, at least two medical liquids may contain saccharides such as glucose and other components such as local anesthetic.

The content in the third chamber is not limited. In Embodiment 1, the third chamber 33 does not contain liquid. The purpose of having the third chamber is not limited. In Embodiment 1, the third chamber 33 is provided as a safety space part. For example, a third chamber 33 may contain a third medical liquid. In another example, a third chamber 33 is not formed.

Embodiment 2

A reservoir assembly 1 of Embodiment 1 can be prepared as follows.

The first chamber 31 holds the first medical liquid, which is prepared by introducing the first medical liquid into the first chamber 31 through the first inlet opening of the multi-chamber reservoir 3 according to Embodiment 1 and sealing the first inlet opening. The sealed first inlet opening 303 forms a part of the inner surface **37*a* of the first chamber 31. Similarly, the second medical liquid is introduced into the second chamber 32. The sealed second inlet opening 304 forms a part of the inner surface 37*b* of the second chamber 32**.

The multi-chamber reservoir 3 holding the first and second medical liquids is sterilized at 118° C. with steam under high pressure for 16 minutes. The sterilization releases carbon dioxide ($CO_2$), generated from bicarbonate ions ($HCO_3^-$) in the second medical liquid held in the second chamber 32, from the multi-chamber reservoir 3. As a result, the pH of the second medical liquid held in the second chamber 32 increases compared to that of the second medical liquid at the preparation. When prepared with a second medical liquid having an increased pH, the cardioplegic solution has a high pH and becomes an alkali solution. The cardioplegic solution being alkali may not achieve the intended purpose and is not preferably used.

The sterilized multi-chamber reservoir 3 is introduced with the oxygen detection agent 5 and the deoxygenation agent 6 into the gas-impermeable outer package 2 through the inlet opening. The deoxygenation agent neither generates nor absorbs carbon dioxide. A mixed gas containing carbon dioxide is filled in the space part 4 between the outer package 2 and the multi-chamber reservoir 3 in order to supply the second medical liquid with bicarbonate ions decreased upon the sterilization. After filling with the mixed gas containing carbon dioxide, the inlet opening of the outer package 2 is sealed to obtain a reservoir assembly 1.

The mixed gas containing carbon dioxide may be filled in an amount so that, after the bicarbonate ion (dissolved carbon dioxide) concentration in the second medical liquid has reached an equilibrium with the carbon dioxide concentration in the space part 4 of the reservoir assembly, the bicarbonate ion concentration of the second medical liquid is within 98 to 102% of the bicarbonate ion concentration in the second medical liquid before being sterilized. For example, when the volume of the second medical liquid is 300 mL, a mixed gas of 550 mL having nitrogen and 1.8% carbon dioxide is filled in the space part 4. The concentration of carbon dioxide to be filled depends on the volume of the second medical liquid containing bicarbonate ions and the sterilizing condition. For example, a mixed gas containing 1 to 3% carbon dioxide is introduced in a volume 1 to 3 times the volume of the second medical liquid containing bicarbonate ions.

The order of introducing the medical liquids is not limited. In Embodiment 2, the second medical liquid is introduced into the second chamber 32 after the first medical liquid is introduced into the first chamber 31. The order to introduce liquids into the respective chamber of a multi-chamber reservoir 3 may be appropriately determined. For example, each liquid may be introduced into the respective chamber at the same time.

Sterilization procedures are not limited. In Embodiment 2, sterilizing is carried out with steam under high pressure. Heating sterilization includes, for example, hot water spray sterilizing, hot water shower sterilizing, and hot water soaking sterilizing. The sterilizing conditions are not limited. In the embodiment, sterilizing with steam under high pressure is carried out at 118° C. for 16 munities.

The packing procedure is not limited. In Embodiment 2, the sterilized multi-chamber reservoir 3 is packed into the gas-impermeable outer package after being sterilized.

The packing procedure is not limited. In Embodiment 2, the sterilized multi-chamber reservoir 3 is packed into the gas-impermeable outer package 2, with the oxygen detection agent 5 and the deoxygenation agent 6 that neither generates nor absorbs carbon dioxide. For example, the multi-chamber reservoir 3 may be packed into the gas-impermeable outer package 2 after the oxygen detection agent 5 and the dioxygen agent 6 that neither generates nor absorbs carbon dioxide are packed into the outer package 2.

The packing procedure is not limited. In Embodiment 2, the mixed gas containing carbon dioxide is filled into the space part 4 after packing the multi-chamber reservoir 3, the oxygen detection agent 5, and the deoxygenation agent 6. For example, a mixed gas containing carbon dioxide may be filled before or at the same time as packing the multi-chamber reservoir 3, the oxygen detection agent 5, and the deoxygenation agent 6. In another example, a mixed gas containing carbon dioxide may be filled by packing the multi-chamber reservoir 3, the oxygen detection agent 5, and the deoxygenation agent 6 into the outer package 2 in a compartment (room) filled with the mixed gas.

The type of gas to be filled in the space part 4 is not limited. In Embodiment 2, a mixed gas of nitrogen and carbon dioxide is used to fill the space part 4. A filling gas may be, for example, carbon dioxide gas alone, a mixed gas of carbon dioxide gas and gas other than nitrogen gas, or a mixed gas of other gas in addition to carbon dioxide gas and nitrogen gas.

The features described in this specification about multi-chamber reservoirs, outer packages, deoxygenation agents, deoxygenation agents that neither generates nor absorbs carbon dioxide, and medical liquids or solutions are also applied to the elements in Embodiments 1 and 2.

The embodiments of the invention include, but are not limited to, the following.

[Item 1] A reservoir assembly for providing a cardioplegic solution, comprising a multi-chamber reservoir; a gas-impermeable outer package packaging the multi-chamber reservoir; an oxygen detection agent and a deoxygenation agent in a space part between the multi-chamber reservoir and the outer package, wherein the deoxygenation agent neither generates nor absorbs carbon dioxide, wherein the multi-chamber reservoir comprises at least a first chamber, a second chamber, and a first separator wall that separates the two chambers, the first chamber holds a first medical liquid, the second chamber holds a second medical liquid containing bicarbonate ions, one or both of the first medical liquid and the second medical liquid contains potassium ions, the cardioplegic solution comprises the first medical liquid and the second medical liquid, and the cardioplegic solution contains bicarbonate ions of 5 to 20 mEq/L and potassium ions of 5 to 35 mEq/L.

[Item 2] The reservoir assembly according to Item 1, wherein the deoxygenation agent includes a cross-linked polymer having carbon-carbon unsaturated bonds.

[Item 3] The reservoir assembly according to Item 1 or 2, wherein the first medical liquid contains magnesium ions, and the cardioplegic solution contains magnesium ions of 2 to 55 mEq/L.

[Item 4] The reservoir assembly according to any one of Items 1 to 3, wherein the first medical liquid contains calcium ions.

[Item 5] The reservoir assembly according to any one of Items 1 to 4, wherein the cardioplegic solution has a pH of 7.6 to 8.

[Item 6] The reservoir assembly according to any one of Items 1 to 5, wherein the volume ratio of the first medical liquid to the second medical liquid is 1:1 to 4:1; the cardioplegic solution contains sodium ions of 100 to 150 mEq/L, potassium ions of 5 to 35 mEq/L, calcium ions of 0.5 to 5 mEq/L, magnesium ions of 2 to 55 mEq/L, and bicarbonate ions of 5 to 20 mEq/L; and the cardioplegic solution has a pH of 7.6 to 8.

[Item 6-1] The reservoir assembly according to Item 6, wherein the cardioplegic solution further contains chloride ions of 100 to 180 mEq/L.

[Item 7] The reservoir assembly according to Item 6, wherein the first medical liquid contains sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg; and the second medical liquid contains sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg.

[Item 7-1] The reservoir assembly according to Item 7, wherein the first medical liquid further contains chloride ions of 179.1±20 mEq/L.

[Item 7-2] The reservoir assembly according to Item 7 or 7-1, wherein the second medical liquid further contains chloride ions of 116.7±10 mEq/L.

[Item 8] A reservoir assembly for providing a cardioplegic solution, comprising a multi-chamber reservoir; a gas-impermeable outer package packaging the multi-chamber reservoir; an oxygen detection agent and a deoxygenation agent in a space part between the multi-chamber reservoir and the outer package, wherein the multi-chamber reservoir comprises at least a first chamber, a second chamber, a third chamber, a first separator wall that separates the first chamber and the second chamber, and a second separator wall that separates the second chamber and the third chamber; the first chamber holds a first medical liquid including sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg; the second chamber holds a second medical liquid including sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg; the volume ratio of the first medical liquid to the second medical liquid is 7:3; the cardioplegic solution comprises the first medical liquid and the second medical liquid, the cardioplegic solution including sodium ions of 110 to 130 mEq/L, potassium ions of 14 to 17 mEq/L, calcium ions of 2 to 3 mEq/L, magnesium ions of 30 to 35 mEq/L, and bicarbonate ions of 8 to 12 mEq/L; the cardioplegic solution has a pH of 7.6 to 8 and osmotic pressure of 275 to 300 mOsm/kg; and the deoxygenation agent includes a cross-linked polymer having carbon-carbon unsaturated bonds.

[Item 8-1] The reservoir assembly according to Item 8, wherein the first medical liquid further contains chloride ions of 179.1±20 mEq/L.

[Item 8-2] The reservoir assembly according to Item 8 or 8-1, wherein the second medical liquid further contains chloride ions of 116.7±10 mEq/L.

[Item 8-3] The reservoir assembly according to Item 8, 8-1, or 8-2, wherein the cardioplegic solution further contains chloride ions of 150 to 170 mEq/L.

[Item 9] A method for manufacturing a reservoir assembly for providing a cardioplegic solution, comprising: sterilizing a multi-chamber reservoir comprising at least a first chamber that holds a first medical liquid, a second chamber that holds a second medical liquid containing bicarbonate ions, and a first separator wall that separates the two chambers; packaging the multi-chamber reservoir, an oxygen detection agent, and a deoxygenation agent in a gas-impermeable outer package, wherein the deoxygenation agent neither generates nor absorbs carbon dioxide; filling carbon dioxide into the outer package; and sealing the outer package after filling carbon dioxide; wherein one or both of the first medical liquid and the second medical liquid contains potassium ions; the cardioplegic solution comprises the first medical liquid and the second medical liquid; and the cardioplegic solution contains bicarbonate ions of 5 to 20 mEq/L and potassium ions of 5 to 35 mEq/L.

[Item 10] The method according to Item 9, wherein the deoxygenation agent includes a cross-linked polymer having carbon-carbon unsaturated bonds.

[Item 11] The method according to Item 9 or 10, wherein the first medical liquid contains magnesium ions, and the cardioplegic solution contains magnesium ions of 2 to 55 mEq/L.

[Item 12] The method according to any one of Items 9 to 11, wherein the first medical liquid contains calcium ions.

[Item 13] The method according to any one of Items 9 to 12, wherein the cardioplegic solution has a pH of 7.6 to 8.

[Item 14] The method according to any one of Items 9 to 13, wherein the volume ratio of the first medical liquid to the second medical liquid is 1:1 to 4:1; the cardioplegic solution contains sodium ions of 100 to 150 mEq/L, potassium ions of 5 to 35 mEq/L, calcium ions of 0.5 to 5 mEq/L, magnesium ions of 2 to 55 mEq/L, and bicarbonate ions of 5 to 20 mEq/L; and the cardioplegic solution has a pH of 7.6 to 8.

[Item 14-1] The method according to Item 14, wherein the cardioplegic solution further contains chloride ions of 100 to 180 mEq/L.

[Item 15] The method according to Item 14, wherein the first medical liquid contains sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg; and the second medical liquid contains sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg.

[Item 15-1] The method according to Item 15, wherein the first medical liquid further contains chloride ions of 179.1±20 mEq/L.

[Item 15-2] The method according to Item 15 or 15-1, wherein the second medical liquid further contains chloride ions of 116.7±10 mEq/L.

[Item 16] A method for manufacturing a reservoir assembly for providing a cardioplegic solution, comprising: sterilizing a multi-chamber reservoir that holds a first medical liquid and a second medical liquid containing bicarbonate ions; packaging the sterilized multi-chamber reservoir in a gas-impermeable outer package; and sealing the outer package that packs the multi-chamber reservoir to produce a reservoir assembly, wherein an oxygen detection agent and a deoxygenation agent are packed in a space part between the multi-chamber reservoir and the gas-impermeable outer package, wherein the deoxygenation agent neither generates nor absorbs carbon dioxide, wherein carbon dioxide is filled into the outer package, wherein the multi-chamber reservoir comprises at least a first chamber, a second chamber, a third chamber, a first separator wall that separates the first chamber and the second chamber, and a second separator wall that separates the second chamber and the third chamber; the first chamber holds a first medical liquid containing sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg; the second chamber holds a second medical liquid containing sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg; the volume ratio of the first medical liquid to the second medical liquid is 7:3; the cardioplegic solution comprises the first medical liquid and the second medical liquid, the cardioplegic solution containing sodium ions of 110 to 130 mEq/L, potassium ions of 14 to 17 mEq/L, calcium ions of 2 to 3 mEq/L, magnesium ions of 30 to 35 mEq/L, and bicarbonate ions of 8 to 12 mEq/L; the cardioplegic solution has a pH of 7.6 to 8 and osmotic pressure of 275 to 300 mOsm/kg; and the deoxygenation agent includes a cross-linked polymer having carbon-carbon unsaturated bonds.

[Item 16-1] The method according to Item 16, wherein the first medical liquid further contains chloride ions of 179.1±20 mEq/L.

[Item 16-2] The method according to Item 16, or 16-1, wherein the second medical liquid further contains chloride ions of 116.7±10 mEq/L.

[Item 16-3] The method according to Item 16, 16-1, or 16-2, wherein the cardioplegic solution further contains chloride ions of 150 to 170 mEq/L.

[Item 17] The method according to any one of Items 9 to 16, wherein filling carbon dioxide comprises filling the outer package with carbon dioxide in an amount so that, after the bicarbonate ion concentration in the second medical liquid has reached an equilibrium with the carbon dioxide concentration in a space part between the multi-chamber reservoir and the outer package, the second medical liquid has a bicarbonate ion concentration within 98% to 102% of the bicarbonate ion concentration before being sterilized.

[Item 18] The method according to any one of Items 8 to 17, wherein sterilizing comprises sterilizing with steam at high pressure.

[Item 19] The reservoir assembly according to any one of Items 1-8, wherein the cardioplegic solution contains sodium ion ($Na^+$) of 120 mEq/L, potassium ions ($K^+$) of 16 mEq/L, calcium ions ($Ca^{2+}$) 2.4 mEq/L, magnesium ions ($Mg^{2+}$) 32 mEq/L, and bicarbonate ions ($HCO_3^-$) of 10 mEq/L.

[Item 19-1] The reservoir assembly according to Item 19, wherein the cardioplegic solution further contains chloride ions ($Cl^-$) of 160.4 mEq/L.

[Item 20] The method according to any one of Items 9-17, wherein the cardioplegic solution contains sodium ions ($Na^+$) of 120 mEq/L, potassium ions ($K^+$) of 16 mEq/L, calcium ions ($Ca^{2+}$) of 2.4 mEq/L, magnesium ions ($Mg^{2+}$) of 32 mEq/L, and bicarbonate ions ($HCO_3^-$) of 10 mEq/L.

[Item 20-1] The method according to Item 20, wherein the cardioplegic solution further contains chloride ions (CL) of 160.4 mEq/L.

The particular examples will be described below. However, these examples are merely given to preferred embodiments of the present invention and do not limit the scope of the invention recited in the accompanying claims in any manner.

EXAMPLES

Test Example 1

1. Preparation of Medical Solution (Test Example 1)

Miotecter® Coronary Vascular Injection (Kyowa Criti-Care Co., Ltd.) is a market product of St. Thomas' II solution being a cardioplegic solution is provided as a two-component formulation for providing the cardioplegic solution at the time of use. The formulation comprises a plastic container that holds the first medical liquid (495 mL) and a glass ampule that holds the second medical liquid (5 mL) and provides the cardioplegic solution by mixing the first medical liquid and the second medical liquid at the time of use. The following table shows the components in the first and second medical liquids and each concentration (theoretical value) of ion species in the mixed solution (hereinafter referred to as "Miotecter® cardioplegic solution") provided by the Miotecter® cardioplegic solution kit.

TABLE 1

| Components in the first and second medical liquids of Miotecter ® cardioplegic solution kit [mg] | | | | |
|---|---|---|---|---|
| First medical liquid | | | | Second medical liquid |
| Sodium chloride (NaCl) | Potassium chloride (KCl) | Magnesium chloride ($MgCl_2$•$6H_2O$) | Calcium chloride hydrate ($CaCl_2$•$2H_2O$) | Sodium bicarbonate ($NaHCO_3$) |
| 3214.2 | 596.4 | 1626.4 | 88.2 | 420 |

| Ion concentrations in Miotecter ® cardioplegic solution [mEq/L] (theoretical valu) | | | | | |
|---|---|---|---|---|---|
| $Na^+$ | $K^+$ | $Mg^{2+}$ | $Ca^{2+}$ | $HCO_3^-$ | $Cl^-$ |
| 120 | 16 | 32 | 2.4 | 10 | 160.4 |

The first medical liquid (pH 3.8) and the second medical liquid were appropriately prepared so that the Miotecter® cardioplegic solution contained the ion species. The first and second liquids were filtrated and then introduced into respective chamber of a double bag container (multi-chamber container) having a capacity of 1 L.

The double bag container of 1 L capacity has a first chamber (volume 700 mL), a second chamber (volume 300 mL), a separator wall that separates the first chamber and the second chamber, and a port part in the second chamber. The port part allows the liquid to flow through in and out of the container.

The following two matters were considered when the first and second medical liquids were prepared with components to include the ion species for the Miotecter® cardioplegic solution. Calcium or magnesium ion should be included in a different medical liquid(s), separately from bicarbonate ion. When the calcium ion or magnesium ion is included in a medical liquid with bicarbonate ion, insoluble particles are formed. Next, the medical liquid in a chamber near the port part should contain sodium and potassium ions at concentrations within normal ion concentrations in serum (plasma) and have an osmotic pressure of 275 to 300 mOsm/kg (the ratio of the osmotic pressure (to physiological saline solution) is about 1).

The following tables show the components and ion concentrations in the first and second medical liquids.

TABLE 2

| | Component | Amount [g] |
|---|---|---|
| First medical liquid (700 mL) (pH 3.8) | Sodium chloride (NaCl) | 4.4531 |
| | Potassium chloride (KCl) | 1.1033 |
| | Calcium chloride dihydrate ($CaCl_2$•$2H_2O$) | 0.1764 |
| | Magnesium chloride hexahydrate ($MgCl_2$•$6H_2O$) | 3.2528 |
| | pH adjuster (dilute hydrochloric acid) | q.s. |
| Second medical liquid (300 mL) | Sodium chloride (NaCl) | 1.9753 |
| | Potassium chloride (KCl) | 0.0895 |
| | Sodium bicarbonate ($NaHCO_3$) | 0.84 |

TABLE 3

| | Ion species | Conc. [mEq/L] |
|---|---|---|
| First medical liquid (700 mL) (pH 3.8) | $Na^+$ | 108.9 |
| | $K^+$ | 21.1 |
| | $Ca^{2+}$ | 3.4 |
| | $Mg^{2+}$ | 45.7 |
| | $Cl^-$ | 179.1 * |
| Second medical liquid (300 mL) | $Na^+$ | 146 |
| | $K^+$ | 4 |
| | $Cl^-$ | 116.7 |
| | $HCO_3^-$ | 33.3 |

* Does not count $Cl^-$ ions derived from the pH adjuster (dilute hydrochloric acid)

2. Preparation of a Reservoir Assembly (Test Example 1)

A plug was inserted into the port part of a double bag container of 1 L capacity and welded to seal. The first and second medical liquids were introduced into the first and second chambers through the respective inlet opening. The inlet openings were sealed with an auto-sealer device (FUJI IMPULSE Co., Ltd., FA-450-5W). The double bag container was sterilized with a sterilizer (HISAKA WORKS, Ltd., GPS-100/10SPXG). The sterilized double bag container was packed in a gas-impermeable outer package. A mixed gas of 550 mL containing nitrogen gas and carbon dioxide gas (0 to 10%) was filled into the space part between the double bag container and the outer package. The inlet opening of the outer package was sealed to produce a reservoir assembly.

3. Stability Test (Test Example 1)

The produced reservoir assembly was stored for two weeks at 25±2° C. and 60±5% RH. The carbon dioxide gas concentration in the space part and bicarbonate ion concentration of the second medical liquid were measured for checking the stability (n=2). Carbon dioxide gas concentration reached a plateau within 10 days after manufacturing the reservoir assembly. Accordingly, the storage period was set to be two weeks.

The following table shows the gas concentrations of carbon dioxide in the space part (immediately and 2 weeks after manufacturing), the pH values of the respective liquids after the 2-week storage, and the concentration ratios of bicarbonate ions in the second medical liquid after the 2-week storage.

TABLE 4

| $CO_2$ conc. [%]*1 | | pH value*2 after two-week storage | | | Conc. ratio of Bicarbonate ions in the second medical liquid [%]*3 | Is the pH of the cardioplegic solution acceptable? |
|---|---|---|---|---|---|---|
| Immediately after manufacturing | Two weeks after manufacturing | First medical liquid | Second medical liquid | Cardioplegic solution (mixed solution) | | |
| 0.0 | 0.2 | 3.8 | 8.6 | 8.1 | 97.5 | NO |
| 0.0 | 0.2 | 3.8 | 8.5 | 8.1 | 97.5 | NO |
| 1.0 | 0.4 | 3.8 | 8.4 | 7.9 | 98.9 | YES |
| 1.0 | 0.4 | 3.8 | 8.4 | 7.9 | 98.6 | YES |
| 2.9 | 0.9 | 3.8 | 8.2 | 7.6 | 99.6 | YES |
| 3.1 | 0.9 | 3.8 | 8.2 | 7.6 | 100.0 | YES |
| 5.8 | 1.9 | 3.8 | 7.9 | 7.3 | 101.1 | NO |
| 6.2 | 2.0 | 3.8 | 7.9 | 7.3 | 101.8 | NO |
| 10.1 | 3.4 | 3.8 | 7.6 | 7.1 | 102.5 | NO |
| 10.1 | 3.4 | 3.8 | 7.6 | 7.1 | 103.2 | NO |

*1 $O_2/CO_2$ analyzer (Dansensor Co. Ltd., CheckMate 3)
*2 pH meter (DKK-TOA Cop., HM-30R)
*3 The conc. ratio means [Concentration of bicarbonate ions in the second medical liquid after 2-week storage (w/v %)]/[Concentration of bicarbonate ions in the second medical liquid at preparation (w/v %)] × 100. The concentration of bicarbonate ions in the second medical liquid at preparation was 0.280 (w/v %).

The carbon dioxide gas concentration in the space part was zero immediately after filling the space part with nitrogen gas containing 0% carbon dioxide and came to be 0.2% two weeks later. This indicates that carbon dioxide was generated from bicarbonate ions in the second medical liquid and leaked from the multi-chamber reservoir to the space part. The decrease in the concentration ratio of bicarbonate ions in the second medical liquid increases pH of the cardioplegic solution. In fact, when a mixed gas containing 0% carbon dioxide was used, the cardioplegic solution prepared by mixing the first and second medical liquids before the sterilization process had a pH of 7.75, which increased to 8.1 in the cardioplegic solution prepared by mixing the two liquids after the two weeks storage. The pH value of the cardioplegic solution manufactured by filling with nitrogen gas containing 0% carbon dioxide exceeded the acceptable pH range of the Miotecter® cardioplegic solution, from 7.6 to 8.0.

The carbon dioxide gas concentration in the space part was 1% immediately after filling the space part with a mixed gas containing 1% carbon dioxide and decreased to 0.4% two weeks later. This implied a possibility that carbon dioxide in the space part dissolved into the second medical liquid. In fact, the concentration ratio of bicarbonate ions in the second medical liquid after the two weeks storage was 97.5%, while it was 98.9/98.6% when the gas containing 1% carbon dioxide was used. The increased concentration ratio of bicarbonate ions in the second medical liquid after the two weeks storage caused a decrease in the pH to 8.4 of the cardiopledic solution compared to the pH 8.6/8.5 when the gas with 0% carbon dioxide was used. The result supports the possibility that the carbon dioxide in the space part supplied bicarbonate ions in the second medical liquid. The pH value of the cardioplegic solution manufactured by filling the space part with a mixed gas containing 1% carbon dioxide was 7.9, which is within the acceptable pH range of the Miotecter® cardioplegic solution, from 7.6 to 8.0.

The concentration ratio of bicarbonate ions in the second medical liquid after the two weeks storage was 98.9/98.6%, which was below 100% before sterilizing even though bicarbonate ions in the second medical liquid were supplied from the carbon dioxide in the space part filled with a mixed gas containing 1% carbon dioxide. This suggests that the carbon dioxide introduced to the space part did not sufficiently supply bicarbonate ions corresponding to the carbon dioxide released upon the sterilization.

The result of using the mixed gas containing 1% carbon dioxide implies a possibility that a higher concentration of carbon dioxide would sufficiently supply bicarbonate ions corresponding to the carbon dioxide released upon sterilizing. In fact, when a mixed gas with 3% carbon dioxide was used, the second medical liquid indicated the concentration ratio of bicarbonate ions was 99.6/100%, which corresponded to the bicarbonate ion contents (100%) before the sterilization process. The result indicates that 3% carbon dioxide could sufficiently supply during storage the number of bicarbonate ions equal to the carbon dioxide released from the second medical liquid upon the sterilization. The cardioplegic solution produced by mixing with the first and second medical liquids equilibrated under 3% carbon dioxide had a pH of 7.6, which corresponds to the pH 7.75 of the cardioplegic solution in Test Example 1 where the sterilization was not carried out.

The results in Test Example 1 indicate that when carbon dioxide is used at a concentration and volume appropriate for filling the space part after packing the sterilized multi-chamber container in the outer package, the carbon dioxide can sufficiently supply the number of carbonate ions equal to carbon dioxide released from the second medical liquid containing bicarbonate ions upon the sterilization, and thereby can provide a cardioplegic solution having a required pH range.

Test Example 2

Test Example 1 was carried out under the condition that rips such as a pinhole might unlikely occur in the gas-impermeable outer package. Test Example 1 accordingly did not use a pinhole detection system (for example, a combination of a deoxygenation agent and an oxygen detection agent). In reality, rips such as a pinhole may occur in the outer package due to friction during transporting the reservoir assemblies that provide the cardioplegic solutions after manufacturing to the place of use. When rips such as a pinhole occur in the gas-impermeable outer package, the gas in the space part between the multi-chamber reservoir and the outer package is gradually replaced with the air outside the reservoir assembly. Such reservoir assemblies may not provide the required cardioplegic solutions. Accordingly, detecting pinholes is essential for a reservoir assembly that holds the second medical liquid containing bicarbonate ions.

Test Example 2 uses a pinhole detection system in a reservoir assembly for providing a cardioplegic solution.

A reservoir assembly for providing a medical solution containing bicarbonate ions uses a deoxygenation agent that generates carbon dioxide to sufficiently stabilize a carbonate ion-containing medical liquid in the reservoir assembly (Patent Literature 1). Patent Literature 1 discloses the carbon dioxide-generating deoxygenation agent as an alternative method of using carbon dioxide. Accordingly, Test Example 2 uses, instead of the use of a mixed gas containing carbon dioxide in Test Example 1, a pinhole detection system that utilizes a combination of an oxygen detection agent and a deoxygenation agent that generates carbon dioxide.

1. Preparation of Reservoir Assembly (Test Example 2) A reservoir assembly (Test Example 2) was prepared according to substantially the same method as Test Example 1 except for the following: the pH of the first medical liquid was not adjusted which gave the liquid of pH 5.7, and was adjusted to give the liquids of pH 4.0 and 3.6; the space part between the multi-chamber reservoir and the outer package was filled with nitrogen gas (0% carbon dioxide) in the volume of 540 mL; and a carbon dioxide-generating deoxygenation agent (Mitsubishi Gas Chemical Company, Inc., GE-100RXF) and an oxygen detection agent were introduced into the space part.

2. Stability Test (Test Example 2)

A stability test was carried out according to substantially the same method as Test Example 1 except that the storage period changed from two weeks to three weeks (n=2). The following table shows the gas concentrations of carbon dioxide and oxygen (immediately and three weeks after manufacturing) and the pH values of the respective liquids after the three weeks storage.

TABLE 5

| pH value of the first medical liquid | Gas conc. [%] Immediately after manufacturing $CO_2$ | Gas conc. [%] Immediately after manufacturing $O_2$ | Gas conc. [%] Three weeks after manufacturing $CO_2$ | Gas conc. [%] Three weeks after manufacturing $O_2$ | pH value after the thre weeks storage First medical liquid | pH value after the thre weeks storage Second medical liquid | pH value after the thre weeks storage Mixed solution | Is the pH of the cardioplegic solution acceptable? |
|---|---|---|---|---|---|---|---|---|
| 3.6 | 0.0 | 0.24 | 2.0 | 0.02 | 3.6 | 7.9 | 7.3 | NO |
| | 0.0 | 0.23 | 2.3 | 0.02 | 3.6 | 7.9 | 7.2 | NO |
| 4.0 | 0.0 | 0.22 | —*1 | — | — | — | — | — |
| | 0.0 | 0.41 | 2.8 | 0.02 | 4.0 | 7.8 | 7.2 | NO |
| 5.7 | 0.0 | 0.54 | 1.9 | 0.01 | 4.8 | 7.9 | 7.4 | NO |
| | 0.0 | 0.49 | 1.9 | 0.02 | 4.8 | 7.9 | 7.4 | NO |

*1 The test was discontinued due to the occurrence of a pinhole(s).

The carbon dioxide concentration in the space part increased from 0% to 1.9%-2.8% during the three weeks storage regardless of the difference in the pH value of the first medical liquid. The oxygen concentration decreased from 0.22-0.54% to 0.01-0.02%. These results indicate that the carbon dioxide-generating deoxygenation agent used in Test Example 2 absorbs oxygen while releasing carbon dioxide.

The pH of the second medical liquid decreased from 8.6/8.5 (see the results in Test Example 1, 0% carbon dioxide) to 7.8 to 7.9. This result indicates that the carbon dioxide-generating deoxygenation agent released carbon dioxide, which dissolved in the second medical liquid and supplied carbonate ions. The cardioplegic solution (mixed solution) produced by mixing the first and second liquids after the three weeks storage had a pH of 7.2 to 7.4, which was below the acceptable pH range of the Miotecter® cardioplegic solution (pH of 7.6 to 8.0).

Test Example 2 used a pinhole detection system (a combination of an oxygen detection agent and a carbon dioxide-generating deoxygenation agent) under the condition where bicarbonate ions are supplied to restore the number of bicarbonate ions equal to the carbon dioxide released from the second medical liquid in the sterilization step. However, the carbon dioxide-generating deoxygenation agent supplied much bicarbonate ions than the desired amount to the second medical liquid during the three weeks storage, resulting in a cardioplegic solution whose pH was below the acceptable pH range of the Miotecter® cardioplegic solution.

The result indicates that a carbon dioxide-generating deoxygenation agent in a pinhole detection system causes a problem in a reservoir assembly providing a medical solution whose concentration of bicarbonate ions is low (10 mEq/mL) such as St. Thomas' II solution, while the deoxygenation agent in a pinhole detection system does not cause any particular problems in dialysis solutions or substitution solutions whose concentration of bicarbonate ions is relatively high (Fuso Pharmaceutical Industries, Ltd., Sublood®-BSG (bicarbonate ion concentration: about 35 mEq/mL)).

The use of pinhole detection systems with a carbon dioxide-generating deoxygenation agent was problematic. This is probably caused by the higher volume of carbon dioxide generated than the predetermined amount. It also implies a possibility that the volume of generated carbon dioxide depends on the concentration of oxygen gas in the space part. In fact, when the oxygen gas concentration immediately after manufacturing the reservoir assembly with a first medical liquid of pH 3.6 was 0.24 [%], the carbon dioxide concentration after the three weeks storage was 2.0 [%]. When the oxygen gas concentration immediately after manufacturing the reservoir assembly with a first medical liquid of pH 4.0 was as high as 0.41 [%], the carbon dioxide gas concentration after the three weeks storage was also as high as 2.8 [%]. These results support the possibility that the oxygen concentration in the space part affects the volume of the carbon dioxide generated during the storage.

These results suggest that the quality of a product holding the second medical liquid formulation whose concentration of bicarbonate ions is relatively low cannot be easily ensured by using a carbon dioxide-generating deoxygenation agent in a pinhole detection system.

Test Example 3

Test Example 1 showed that carbon dioxide introduced into the space part between the multi-chamber reservoir and the outer package could supply bicarbonate ions decreased by the sterilization, resulting in the desired cardioplegic solution. Test Example 2 used a carbon dioxide-generating deoxygenation agent in a pinhole detection system in order to supply carbon dioxide to the second medical liquid. However, it was showed that the use of the carbon dioxide-generating deoxygenation agent caused a problem in a reservoir assembly that holds the bicarbonate ion-containing second medical liquid whose concentration of bicarbonate ions are relatively low.

Test Example 3 introduced carbon dioxide into the space part between the multi-chamber reservoir and the outer package, and used a deoxygenation agent that does not generate carbon dioxide (carbon dioxide non-generating deoxygenation agent) in the pinhole detection system instead of the carbon dioxide-generating deoxygenation agent.

1. Preparation of Reservoir Assembly (Test Example 3)

A reservoir assembly (Test Example 3) was prepared according to substantially the same method as Test Example 1 except for the following: the first medical liquid was adjusted to have a pH of 4.0 or 3.6; and a carbon dioxide non-generating deoxygenation agent (Mitsubishi Gas Chemical Company, Inc., ZH-100R) and an oxygen detection agent were introduced into the space part between the multi-chamber reservoir and the outer package.

2. Stability Test (Test Example 3)

A stability test was carried out according to substantially the same method as Test Example 1 (n=2). The following table shows the gas concentrations of carbon dioxide and oxygen (immediately and two weeks after manufacturing) and the pH values of the respective liquids after the two weeks storage.

TABLE 6

| pH value of First medical liquid | Gas conc. [%] Immediately after manufacturing $CO_2$ | $O_2$ | Two weeks later $CO_2$ | $O_2$ | pH value after the two weeks storage First medical liquid | Second medical liquid | Mixed solution | Is the pH of the cardioplegic solution acceptable? |
|---|---|---|---|---|---|---|---|---|
| 3.6 | 1.1 | 0.33 | 0.0 | 0.00 | 3.6 | 8.6 | 8.1 | NO |
| | 1.1 | 0.14 | 0.0 | 0.00 | 3.6 | 8.6 | 8.1 | NO |
| | 3.3 | 0.54 | 0.0 | 0.00 | 3.6 | 8.6 | 8.1 | NO |
| | 3.0 | 0.17 | 0.0 | 0.00 | 3.6 | 8.6 | 8.1 | NO |
| | 6.2 | 1.10 | 0.0 | 0.00 | 3.6 | 8.6 | 8.0 | NO |
| | 6.1 | 0.99 | 0.0 | 0.00 | 3.6 | 8.6 | 8.0 | NO |
| 4.0 | 0.9 | 2.28 | 0.0 | 0.00 | 4.0 | 8.6 | 8.2 | NO |
| | 0.9 | 0.32 | 0.0 | 0.00 | 4.0 | 8.6 | 8.2 | NO |
| | 3.4 | 0.17 | 0.0 | 0.00 | 4.0 | 8.6 | 8.2 | NO |
| | 3.4 | 0.18 | 0.0 | 0.00 | 4.0 | 8.6 | 8.2 | NO |
| | 6.3 | 1.02 | 0.0 | 0.00 | 4.0 | 8.6 | 8.1 | NO |
| | 6.4 | 0.16 | 0.0 | 0.00 | 4.0 | 8.5 | 8.1 | NO |

The carbon dioxide non-generating deoxygenation agent used in Test Example 3 rendered the oxygen existed in the space part immediately after manufacturing the reservoir assembly to 0% two weeks later. The carbon dioxide introduced in the manufacturing processes also came to 0% two weeks later. These results indicate that the carbon dioxide non-generating deoxygenation agent absorbs both oxygen and carbon dioxide.

Because the deoxygenation agent absorbed the carbon dioxide introduced into the space part, bicarbonate ions were not supplied in the second medical liquid, resulting in a cardioplegic solution having a pH of 8.0 and 8.2, which are both over the acceptable pH range of the Miotecter® cardioplegic solution (pH of 7.6 to 8.0).

A different carbon dioxide non-generating deoxygenation agent (Mitsubishi Gas Chemical Company, Inc., GLS-100) was also tested in Test Example 3. The deoxygenation agent also absorbed carbon dioxide and oxygen, resulting in a cardioplegic solution having a pH over the acceptable pH range of the Miotecter® cardioplegic solution.

These results suggest that a carbon dioxide non-generating deoxygenation agent (deoxygenation agent that absorbs carbon dioxide) in a pinhole detection system causes a problem in a reservoir assembly that holds the second medical liquid whose concentration of bicarbonate ions are relatively low.

Example 1

The results of Test Examples 1 to 3 suggest that a reservoir assembly that holds the second medical liquid whose concentration of bicarbonate ions is relatively low may be manufactured by filling the space part with carbon dioxide to supply bicarbonate ions equivalent to carbon dioxide released from the bicarbonate ion-containing second medical liquid in the sterilization process, and by using a deoxygenation agent that does not affect the concentration of carbon dioxide filled in the space part (i.e., a deoxygenation agent neither generating nor absorbing carbon dioxygen).

1. Deoxygenation Agent that Neither Generates Nor Absorbs Carbon Dioxide

EXAMPLE 1 uses a deoxygenation agent that neither generates carbon dioxide (generating no carbon dioxide) nor absorbs carbon dioxide (absorbing no carbon dioxide) named AGELESS GP (Mitsubishi Gas Chemical Company, Inc.).

First, the deoxygenation agent that neither generates nor absorbs carbon dioxide was tested for whether the agent absorbs oxygen without generating or absorbing carbon dioxide. The deoxygenation agent was placed inside a gas-impermeable outer package. Then, a mixed gas (540 mL) composed of 2.5% carbon dioxide/97.5% nitrogen (440 mL) and the air (100 mL) was introduced into the outer package, and the outer package was sealed. The concentrations of carbon dioxide [%] and oxygen [%] were measured by the $O_2/CO_2$ analyzer (Dansensor Co. Ltd., CheckMate 3) at three days and seven days after sealing. The measurement results are shown in the table below.

TABLE 7

| | Deoxygenation agent that neither generates nor absorbs carbon dioxide | | | | | |
|---|---|---|---|---|---|---|
| | Immediately after sealing | | 3 days later | | 7 days later | |
| | $CO_2$ | $O_2$ | $CO_2$ | $O_2$ | $CO_2$ | $O_2$ |
| Presence | 2.0 | 3.84 | 2.1 | 0.034 | 2.2 | 0.033 |
| | 2.0 | 3.94 | 2.1 | 0.033 | 2.2 | 0.034 |
| | 2.0 | 4.02 | 2.1 | 0.033 | 2.1 | 0.033 |
| Absence | 1.9 | 3.92 | 1.9 | 3.96 | 1.9 | 3.97 |

The table shows that carbon dioxide concentrations [%] did not change three and seven days after sealing the outer package in which the deoxygenation agent that neither generates nor absorbs carbon dioxide was incorporated. In contrast, the concentration of oxygen [%] came to be below 0.1 [%]. Thus, it was confirmed that the deoxygenation agent absorbs oxygen without generating or absorbing carbon dioxide.

2. Preparation of Reservoir Assembly (Example 1)

A reservoir assembly (Example 1) was prepared according to substantially the same method as Test Example 1 except for the following: a deoxygenation agent that neither generates nor absorbs carbon dioxide (Mitsubishi Gas Chemical Company, Inc.) and an oxygen detection agent (AGELESS-EYE, Mitsubishi Gas Chemical Company, Inc.) were placed in the space part between the multi-chamber reservoir and the outer package; and the space part was filled with a mixed gas of nitrogen and 2% carbon dioxide in the volume of 400 mL, 500 mL, 600 mL, or 700 mL.

3. Preparation of Reservoir Assembly (Comparative Example 1)

A reservoir assembly (Comparative Example 1) was prepared according to substantially the same method as Example 1 except for the deoxygenation agent was not introduced inside the outer package.

4. Stability Test (Example 1 and Comparative Example 1)

A stability test was carried out for the reservoir assemblies of Example 1 (n=3) and Comparative Example 1 (n=2) according to the same method as Test Example 1. The following table shows the gas concentrations of carbon dioxide and oxygen in the space part between the multi-chamber reservoir and the outer package (immediately and two weeks after manufacturing the reservoir assemblies), the respective liquids' pH values after the two weeks storage, and the concentration ratios of bicarbonate ions in the second medical liquid.

TABLE 8

| | Volume of filled gas | Gas conc. [%] | | | | pH value after the two weeks storage | | | Conc. ratio of Bicarbonate ions in the second medical liquid [%]*1 | Is the pH of the cardioplegic solution acceptable? |
|---|---|---|---|---|---|---|---|---|---|---|
| | | Immediately after manufacturing | | Two weeks later | | First medical liquid | Second medical liquid | Mixed solution | | |
| | [mL] | $CO_2$ | $O_2$ | $CO_2$ | $O_2$ | | | | | |
| EXAMPLE 1 | 400 | 1.8 | 0.25 | 0.6 | 0.06 | 3.8 | 8.3 | 7.8 | 98.2 | YES |
| | | 1.8 | 0.42 | 0.6 | 1.06 | 3.8 | 8.3 | 7.7 | 98.8 | YES |
| | | 1.8 | 0.32 | 0.6 | 0.06 | 3.8 | 8.3 | 7.8 | 98.9 | YES |

TABLE 8-continued

| | Volume of filled gas [mL] | Gas conc. [%] Immediately after manufacturing $CO_2$ | $O_2$ | Two weeks later $CO_2$ | $O_2$ | pH value after the two weeks storage First medical liquid | Second medical liquid | Mixed solution | Conc. ratio of Bicarbonate ions in the second medical liquid [%]*1 | Is the pH of the cardioplegic solution acceptable? |
|---|---|---|---|---|---|---|---|---|---|---|
| | 500 | 1.8 | 0.31 | 0.6 | 0.04 | 3.8 | 8.3 | 7.7 | 98.8 | YES |
| | | 1.8 | 0.31 | 0.6 | 0.04 | 3.8 | 8.3 | 7.7 | 99.5 | YES |
| | | 1.8 | 0.46 | 0.7 | 0.05 | 3.8 | 8.3 | 7.7 | 99.3 | YES |
| | 600 | 1.8 | 0.29 | 0.7 | 0.05 | 3.8 | 8.3 | 7.7 | 98.7 | YES |
| | | 1.8 | 0.23 | 0.7 | 0.74 | 3.8 | 8.3 | 7.7 | 99.1 | YES |
| | | 1.8 | 0.32 | 0.7 | 0.05 | 3.8 | 8.3 | 7.7 | 99.3 | YES |
| | 700 | 1.8 | 0.29 | 0.7 | 0.06 | 3.8 | 8.3 | 7.7 | 98.4 | YES |
| | | 1.8 | 0.25 | 0.8 | 0.06 | 3.8 | 8.2 | 7.7 | 99.0 | YES |
| | | 1.8 | 0.56 | 0.7 | 0.06 | 3.8 | 8.2 | 7.7 | 99.3 | YES |
| COMPARATIVE EXAMPLE 1 | 400 | 1.8 | 0.32 | 0.5 | 5.45 | 3.8 | 8.4 | 7.8 | 99.8 | YES |
| | | 1.8 | 0.33 | 0.5 | 5.17 | 3.8 | 8.3 | 7.8 | 99.3 | YES |
| | 500 | 1.8 | 0.37 | 0.5 | 7.79 | 3.8 | 8.3 | 7.8 | 98.7 | YES |
| | | 1.8 | 0.41 | 0.5 | 5.36 | 3.8 | 8.3 | 7.8 | 98.8 | YES |
| | 600 | 1.9 | 0.20 | 0.6 | 3.48 | 3.8 | 8.3 | 7.7 | 100.1 | YES |
| | | 1.9 | 0.20 | 0.6 | 3.59 | 3.8 | 8.3 | 7.7 | 99.8 | YES |
| | 700 | 1.9 | 0.20 | 0.7 | 3.64 | 3.8 | 8.3 | 7.7 | 100.0 | YES |
| | | 1.9 | 0.16 | 0.7 | 3.19 | 3.8 | 8.3 | 7.7 | 99.5 | YES |

*1 The conc. ratio means [Concentration of bicarbonate ions in the second medical liquid after 2-week storage (w/v %)]/[Concentration of bicarbonate ions in the second medical liquid at preparation (w/v %)] × 100. The concentration of bicarbonate ions in the second medical liquid at preparation was 0.280 (w/v %).

The oxygen concentrations were lower in Example 1 using the deoxygenation agent than Comparative Example 1 not using the deoxygenation agent. This indicates that the oxygen detection agent enables the detection of a pinhole.

The carbon dioxide concentrations after the two weeks storage were almost the same in Example 1 using the deoxygenation agent as Comparative Example 1 not using the deoxygenation agent. This indicates that the deoxygenation agent substantially does not affect the carbon dioxide concentration in the space part.

Example 2

The reservoir assembly prepared in Example 1 was measured for providing the desired cardioplegic solution steadily.

1. Preparation of Medical Solution

Sodium chloride of 222.66 g, potassium chloride of 55.16 g, calcium chloride dihydrate of 8.82 g, and magnesium chloride hexahydrate of 162.64 g were dissolved in water to produce the first medical liquid (pH 3.8, 35 L). Sodium chloride of 105.36 g, potassium chloride of 4.76 g, and sodium bicarbonate of 44.80 g were dissolved in water to produce the second medical liquid (pH 8.1, 16 L).

2. Preparation of a Reservoir Assembly (Example 2)

A plug was inserted into the port part of a double bag container of 1 L capacity and welded to seal. The first medical liquid (720 mL) and the second medical liquid (310 mL) were respectively filtrated and introduced into each chamber of the double bag container. The inlet openings were sealed.

The double bag container was sterilized with a sterilizer. The sterilized double bag container was packed in a gas-impermeable outer package, together with a deoxygenation agent (Mitsubishi Gas Chemical Company, Inc.) and an oxygen detection agent (AGELESS-EYE, Mitsubishi Gas Chemical Company, Inc.) used in Example 1. A mixed gas of 580 mL containing nitrogen and 2% carbon dioxide was filled in the outer package to produce a reservoir assembly (Example 2).

3. Stability Test

The stability of the liquids holded in the reservoir assembly was tested in the following storage conditions:

Temperature: 40° C.±1° C., Humidity: 75% RH±5% RH Condition (1):

Temperature: 25° C.±2° C., Humidity: 60% RH±5% RH Condition (2):

Bicarbonate ion concentration, pH, osmotic pressure ratio, sub-visible particle, visible particles, and appearances of the liquids were measured (n=2). The liquids stored under Condition (1) were measured at the start and 1, 3, and 6 months after the start and the liquids stored under Condition (2) were measured at the start and 3 months after the start.

4. Results of the Stability Test (1) Bicarbonate Ion Concentration and pH

The pH values were measured for each solution according to the Japanese Pharmacopeia's general test (pH determination). The bicarbonate ion concentration [mEq/L] of the second medical liquid was measured by liquid chromatography with a column (PCI-305S (6 μm 8.0 mm ID×300 mm)). The results are shown in the table below.

TABLE 9

| Liquid | At the start | Condition (1) 1 month later | 3 months later | 6 months later | Condition (2) 3 months later |
|---|---|---|---|---|---|
| First medical liquid | 3.80 | 3.81 | 3.80 | 3.81 | 3.81 |
| | 3.81 | 3.82 | 3.82 | 3.81 | 3.82 |
| Second medical liquid | 8.28 | 8.32 | —*1 | 8.45 | 8.26 |
| | 8.28 | 8.31 | 8.32 | 8.45 | 8.26 |
| Cardioplegic solution (mixed solution) | 7.71 | 7.75 | —*1 | 7.91 | 7.69 |
| | 7.72 | 7.74 | 7.78 | 7.92 | 7.71 |

The bicarbonate ion concentration [mEq/L] of the second medical liquid was measured by liquid chromatography with a column (PCI-305S (6 μm 8.0 mm ID×300 mm)). The measurement results are shown in the table below.

TABLE 10

| Liquid | At the start | Condition (1) 1 month later | 3 months later | 6 months later | Condition (2) 3 months later |
|---|---|---|---|---|---|
| Second | 33.2 | 33.4 | —*[1] | 33.0 | 33.2 |
| medical liquid | 33.4 | 33.7 | 33.1 | 33.1 | 33.4 |

Unit: mEq/L

*[1]The measurement was discontinued due to the occurrence of pinholes.

The results showed that the cardioplegic solution (mixed solution) prepared from the liquids stored under Condition (2) for three months had a pH of 7.69/7.71, which was almost the same as the pH (7.71/7.72) of the solution at the start of measurement. The results showed that the cardioplegic solution (mixed solution) prepared from the liquids stored under Condition (1) for six months had a pH of 7.91/7.92, which was within the acceptable pH range of the Miotecter® cardioplegic solution (pH 7.6 to 8.0).

The results showed that the bicarbonate ion concentration [mEq/L] did not change in the second medical liquid stored under Conditions (1) and (2).

These results indicate that the medical liquids held in the respective chambers of the reservoir assembly prepared according to the application were sufficiently stable in terms of pH and bicarbonate ion concentration.

(2) Osmotic Pressure Ratio

The osmotic pressures were measured for the first and second medical liquid according to the Japanese Pharmacopoeia's general test (osmolarity determination), and osmotic pressure ratios were calculated with the following equation:

Osmotic Pressure Ratio=Osmotic Pressure of a Sample Liquid [mOsm]/the Osmotic Pressure of physiological saline solution [286 mOsm].

The measurement results are shown in the table below.

TABLE 11

| Liquid | At the start | Condition (1) 1 month later | 3 months later | 6 months later | Condition (2) 3 months later |
|---|---|---|---|---|---|
| First medical | 1.09 | 1.06 | 1.07 | 1.07 | 1.07 |
| liquid | 1.09 | 1.07 | 1.08 | 1.08 | 1.07 |
| Second | 0.99 | 0.97 | 0.99 | 0.98 | 0.98 |
| medical liquid | 0.99 | 0.97 | 0.97 | 0.98 | 0.98 |

These results indicate that the medical liquids held in the respective chambers of the reservoir assembly prepared according to the application were sufficiently stable in terms of osmotic pressure ratio.

(3) Sub-Visible Particle

Sub-visible particles in each liquid solution were measured according to the Japanese Pharmacopoeia's general test (Insoluble Particulate Matter Test for Injections, Method 1). The measurement results are shown in the table below. The liquids under Condition (1) were not measured one month after the start.

TABLE 12

| Liquid | Particle size [μm] | At the start | Condition (1) 3 months later | 6 months later | Condition (2) 3 months later |
|---|---|---|---|---|---|
| First | ≥10 | 0 | 1 | 2 | 0 |
| medical | | 0 | 0 | 0 | 1 |
| liquid | ≥25 | 0 | 0 | 0 | 0 |
| | | 0 | 0 | 0 | 0 |
| Second | ≥10 | 0 | 0 | 0 | 0 |
| medical | | 0 | 0 | 0 | 1 |
| liquid | ≥25 | 0 | 0 | 0 | 0 |
| | | 0 | 0 | 0 | 0 |
| Cardioplegic | ≥10 | 0 | 0 | 2 | 0 |
| solution | | 0 | 1 | 0 | 1 |
| (mixed | ≥25 | 0 | 0 | 0 | 0 |
| solution) | | 0 | 0 | 0 | 0 |

These results indicate that the medical liquids held in the respective chambers of the reservoir assembly prepared according to the application were sufficiently stable in terms of sub-visible particle.

(4) Foreign Insoluble Matter

Visible particles in the first and second medical liquids and the mixed solution (cardioplegic solution) were measured according to the Japanese Pharmacopoeia's general method (Foreign Insoluble Matter Test for Injections, Method 1). The results showed no visible particles in the liquids under Conditions (1) and (2). These results indicate that the medical liquids held in the respective chambers of the reservoir assembly prepared according to the application were sufficiently stable in terms of foreign insoluble matter.

(5) Appearances

Appearances of the first and second medical liquids were observed according to Japanese Pharmacopoeia's general rules. The results showed that the appearances of the liquids were clear colorless and were not changed under Conditions (1) and (2). These results indicate that the medical liquids held in the respective chambers of the reservoir assembly prepared according to the application were sufficiently stable in terms of appearances.

EXPLANATION OF REFERENCES

1 Reservoir assembly
2 Gas-impermeable outer package
3 Multi-chamber reservoir
4 Space part
5 Oxygen detection agent
6 Deoxygenation agent that neither generates nor absorbs carbon dioxide
31 First chamber
32 Second chamber
33 Third chamber
34 Plug
35 Port part
36 Outside wall
37*a* Inner surface of first chamber
37*b* Inner surface of second chamber
37*c* Inner surface of third chamber
301 First separator wall
302 Second separator wall
303 Sealed first inlet opening
304 Sealed second inlet opening

The invention claimed is:

1. A method for manufacturing a reservoir assembly for providing a cardioplegic solution, comprising:

sterilizing a multi-chamber reservoir comprising at least a first chamber that holds a first medical liquid containing magnesium ions and calcium ions, a second chamber that holds a second medical liquid containing bicarbonate ions, and a first separator wall that separates the two chambers;

packaging the multi-chamber reservoir, an oxygen detection agent, and a deoxygenation agent in a gas-impermeable outer package, wherein the deoxygenation agent neither generates nor absorbs carbon dioxide;

filling carbon dioxide into the outer package; and sealing the outer package after filling carbon dioxide; wherein one or both of the first medical liquid and the second medical liquid contains potassium ions, the cardioplegic solution is provided by mixing the first medical liquid and the second medical liquid, the cardioplegic solution contains bicarbonate ions of 8 to 12 mEq/L, calcium ions of 0.5 to 5 mEq/L, magnesium ions of 2 to 55 mEq/L, potassium ions of 5 to 35 mEq/L, and sodium ions of 100 to 150 mEq/L, the cardioplegic solution has a pH of 7.6 to 8, and the volume ratio of the first medical liquid to the second medical liquid is 1:1 to 4:1.

2. The method according to claim 1, wherein the deoxygenation agent includes a cross-linked polymer having carbon-carbon unsaturated bonds.

3. The method according to claim 1, wherein carbon dioxide is filled into the outer package in an amount such that, after the bicarbonate ion concentration in the second medical liquid has reached an equilibrium with the carbon dioxide concentration in a space part between the multi-chamber reservoir and the outer package, the bicarbonate ion concentration of the second medical liquid is within 98% to 102% of the bicarbonate ion concentration in the second medical liquid before being sterilized.

4. A method for manufacturing a reservoir assembly for providing a cardioplegic solution, comprising:

sterilizing a multi-chamber reservoir comprising at least a first chamber that holds a first medical liquid containing magnesium ions and calcium ions, a second chamber that holds a second medical liquid containing bicarbonate ions, and a first separator wall that separates the two chambers;

packaging the multi-chamber reservoir, an oxygen detection agent, and a deoxygenation agent in a gas-impermeable outer package, wherein the deoxygenation agent neither generates nor absorbs carbon dioxide;

filling carbon dioxide into the outer package; and sealing the outer package after filling carbon dioxide; wherein the cardioplegic solution is provided by mixing the first medical liquid and the second medical liquid, the cardioplegic solution contains bicarbonate ions of 8 to 12 mEq/L, calcium ions of 0.5 to 5 mEq/L, magnesium ions of 2 to 55 mEq/L, and potassium ions of 5 to 35 mEq/L, the first medical liquid contains sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg, and the second medical liquid contains sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg.

5. A method for manufacturing a reservoir assembly for providing a cardioplegic solution, comprising:

sterilizing a multi-chamber reservoir comprising at least a first chamber that holds a first medical liquid containing magnesium ions and calcium ions, a second chamber that holds a second medical liquid containing bicarbonate ions, and a first separator wall that separates the two chambers;

packaging the multi-chamber reservoir, an oxygen detection agent, and a deoxygenation agent in a gas-impermeable outer package, wherein the deoxygenation agent neither generates nor absorbs carbon dioxide;

filling carbon dioxide into the outer package; and sealing the outer package after filling carbon dioxide; wherein the multi-chamber reservoir comprises at least a first chamber, a second chamber, a third chamber, a first separator wall that separates the first chamber and the second chamber, and a second separator wall that separates the second chamber and the third chamber, the first chamber holds a first medical liquid including sodium ions of 108.9±10 mEq/L, potassium ions of 21.1±2 mEq/L, calcium ions of 3.4±0.3 mEq/L, and magnesium ions of 45.7±5 mEq/L, the first medical liquid having an osmotic pressure of 275 to 300 mOsm/kg, the second chamber holds a second medical liquid including sodium ions of 146±10 mEq/L, potassium ions of 4±0.4 mEq/L, and bicarbonate ions of 33.3±3 mEq/L, the second medical liquid having an osmotic pressure of 275 to 300 mOsm/kg, the volume ratio of the first medical liquid to the second medical liquid is 7:3, the cardioplegic solution is provided by mixing the first medical liquid and the second medical liquid, the cardioplegic solution including sodium ions of 110 to 130 mEq/L, potassium ions of 14 to 17 mEq/L, calcium ions of 2 to 3 mEq/L, magnesium ions of 30 to 35 mEq/L, and bicarbonate ions of 8 to 12 mEq/L, the cardioplegic solution has a pH of 7.6 to 8 and osmotic pressure of 275 to 300 mOsm/kg, and the deoxygenation agent includes a cross-linked polymer having carbon-carbon unsaturated bonds.

6. The method according to claim 4, wherein the deoxygenation agent includes a cross-linked polymer having carbon-carbon unsaturated bonds.

7. The method according to claim 4, wherein the cardioplegic solution has a pH of 7.6 to 8.

8. The method according to claim 4, wherein the volume ratio of the first medical liquid to the second medical liquid is 1:1 to 4:1.

9. The method according to claim 4, wherein carbon dioxide is filled into the outer package in an amount such that, after the bicarbonate ion concentration in the second medical liquid has reached an equilibrium with the carbon dioxide concentration in a space part between the multi-chamber reservoir and the outer package, the bicarbonate ion concentration of the second medical liquid is within 98% to 102% of the bicarbonate ion concentration in the second medical liquid before being sterilized.

10. The method according to claim 5, wherein carbon dioxide is filled into the outer package in an amount such that, after the bicarbonate ion concentration in the second medical liquid has reached an equilibrium with the carbon dioxide concentration in a space part between the multi-chamber reservoir and the outer package, the bicarbonate ion concentration of the second medical liquid is within 98% to 102% of the bicarbonate ion concentration in the second medical liquid before being sterilized.

* * * * *